(12) United States Patent
Kaufmann et al.

(10) Patent No.: US 12,128,242 B2
(45) Date of Patent: Oct. 29, 2024

(54) MODULAR IMPLANT DELIVERY AND POSITIONING SYSTEM

(71) Applicant: IotaMotion, Inc., Iowa City, IA (US)

(72) Inventors: Christopher Kaufmann, Iowa City, IA (US); Parker Reineke, North Liberty, IA (US); Matthew Jackels, Coralville, IA (US); Allan Henslee, Houston, TX (US)

(73) Assignee: IotaMotion, Inc., Iowa City, IA (US)

( * ) Notice: Subject to any disclaimer, the term of this patent is extended or adjusted under 35 U.S.C. 154(b) by 495 days.

(21) Appl. No.: 17/038,916

(22) Filed: Sep. 30, 2020

(65) Prior Publication Data

US 2021/0093869 A1 Apr. 1, 2021

Related U.S. Application Data

(60) Provisional application No. 62/908,505, filed on Sep. 30, 2019.

(51) Int. Cl.
*A61N 1/375* (2006.01)
*A61B 34/30* (2016.01)
(Continued)

(52) U.S. Cl.
CPC ............. *A61N 1/375* (2013.01); *A61B 34/30* (2016.02); *A61N 1/36125* (2013.01); *B25J 9/12* (2013.01);
(Continued)

(58) Field of Classification Search
CPC .......... A61B 17/3468; A61B 2034/301; A61N 1/0534; A61N 1/0551; A61N 1/372
See application file for complete search history.

(56) References Cited

U.S. PATENT DOCUMENTS

| 3,610,877 A | 10/1971 | Driscoll |
|---|---|---|
| 4,383,532 A | 5/1983 | Dickhudt |

(Continued)

FOREIGN PATENT DOCUMENTS

| AU | 2020357745 | 11/2023 |
|---|---|---|
| CN | 110430918 A | 11/2019 |

(Continued)

OTHER PUBLICATIONS

"U.S. Appl. No. 16/486,030, Corrected Notice of Allowability mailed Jan. 12, 2021", 7 pgs.
(Continued)

*Primary Examiner* — Thomas McEvoy
(74) *Attorney, Agent, or Firm* — Schwegman Lundberg & Woessner, P.A.

(57) ABSTRACT

This document discusses, among other things, systems and methods for robotically assisted implantation of an implant in a patient. A system includes an implant-positioning unit configured to engage an elongate member of the implant, and a control console communicatively coupled to the positioning unit. The control console may have a user interface that enables a user to input motion control instructions. The control console may generate a motion control signal, according to a specific motion control instruction, to control the external positioning unit to propel the implant into a target implant site, path or shape. The system may be used to robotically control the delivery and positing of a neuromodulating implant during a spinal stimulator implantation or deep brain stimulator implantation surgery.

14 Claims, 37 Drawing Sheets

(51) Int. Cl.
*A61N 1/36* (2006.01)
*B25J 9/12* (2006.01)
*A61B 17/34* (2006.01)
*A61N 1/05* (2006.01)

(52) U.S. Cl.
CPC ..... *A61B 17/3468* (2013.01); *A61B 2034/301* (2016.02); *A61B 2034/302* (2016.02); *A61N 1/0534* (2013.01); *A61N 1/0551* (2013.01)

(56) References Cited

U.S. PATENT DOCUMENTS

| | | |
|---|---|---|
| 4,532,930 A | 8/1985 | Crosby et al. |
| 4,637,404 A | 1/1987 | Gessman |
| 5,201,765 A | 4/1993 | Netterville et al. |
| 5,306,298 A | 4/1994 | Godley, III et al. |
| 5,593,439 A | 1/1997 | Cummings et al. |
| 5,758,396 A | 6/1998 | Jeon et al. |
| 7,524,320 B2 | 4/2009 | Tierney et al. |
| 7,691,098 B2 | 4/2010 | Wallace et al. |
| 8,010,210 B2 | 8/2011 | Rau et al. |
| 8,229,574 B2 | 7/2012 | Parker et al. |
| 8,583,261 B2 | 11/2013 | Llinas et al. |
| 8,594,799 B2 | 11/2013 | Haller et al. |
| 8,886,331 B2 | 11/2014 | Labadie et al. |
| 9,561,372 B2 | 2/2017 | Jiang et al. |
| 9,675,446 B2 | 6/2017 | Jaber et al. |
| 9,700,408 B1 | 7/2017 | Sataloff |
| 9,986,998 B2 | 6/2018 | Martin et al. |
| 10,085,806 B2 | 10/2018 | Hagn et al. |
| 10,945,761 B2 | 3/2021 | Kaufmann et al. |
| 2003/0171758 A1 | 9/2003 | Gibson et al. |
| 2004/0236390 A1 | 11/2004 | Dadd et al. |
| 2005/0004627 A1 | 1/2005 | Gibson et al. |
| 2005/0245991 A1 | 11/2005 | Faltys et al. |
| 2006/0241723 A1 | 10/2006 | Dadd et al. |
| 2007/0156123 A1 | 7/2007 | Moll et al. |
| 2007/0225787 A1 | 9/2007 | Simaan et al. |
| 2008/0077221 A1 | 3/2008 | Milojevic et al. |
| 2008/0097487 A1* | 4/2008 | Pool ............. A61F 5/003 606/151 |
| 2008/0188931 A1 | 8/2008 | Kwon |
| 2010/0114288 A1 | 5/2010 | Haller et al. |
| 2011/0021903 A1 | 1/2011 | Strommer et al. |
| 2011/0066160 A1 | 3/2011 | Simaan et al. |
| 2011/0106101 A1 | 5/2011 | Tortonese et al. |
| 2011/0264038 A1 | 10/2011 | Fujimoto et al. |
| 2012/0041531 A1 | 2/2012 | Dadd et al. |
| 2012/0071890 A1 | 3/2012 | Taylor et al. |
| 2012/0150293 A1 | 6/2012 | Hoffman et al. |
| 2012/0191107 A1 | 7/2012 | Tanner et al. |
| 2013/0138117 A1 | 5/2013 | Abbott et al. |
| 2013/0245569 A1 | 9/2013 | Jolly et al. |
| 2013/0296884 A1 | 11/2013 | Taylor et al. |
| 2013/0331779 A1 | 12/2013 | Dhanasingh et al. |
| 2014/0135799 A1 | 5/2014 | Henderson |
| 2014/0213988 A1* | 7/2014 | Perouse ............. A61B 17/12 604/288.02 |
| 2014/0222207 A1 | 8/2014 | Bowling et al. |
| 2014/0276391 A1 | 9/2014 | Yu |
| 2014/0350640 A1 | 11/2014 | Patrick et al. |
| 2014/0358174 A1 | 12/2014 | Thenuwara et al. |
| 2015/0032123 A1 | 1/2015 | Jolly et al. |
| 2015/0032124 A1 | 1/2015 | Lenarz et al. |
| 2015/0105795 A1 | 4/2015 | Lenarz et al. |
| 2015/0342445 A1 | 12/2015 | Jones et al. |
| 2016/0045747 A1 | 2/2016 | Jiang et al. |
| 2018/0021568 A1 | 1/2018 | Schachtele et al. |
| 2018/0242967 A1 | 8/2018 | Meade |
| 2019/0029668 A1 | 1/2019 | Meade et al. |
| 2019/0142247 A1 | 5/2019 | Maeda et al. |
| 2019/0282803 A1 | 9/2019 | Hansen et al. |
| 2020/0038106 A1 | 2/2020 | Pieper et al. |
| 2020/0046978 A1 | 2/2020 | Kaufmann et al. |
| 2020/0069386 A1 | 3/2020 | Betsugi et al. |
| 2020/0329950 A1 | 10/2020 | Shear et al. |
| 2020/0337725 A1 | 10/2020 | Kaufmann et al. |
| 2021/0077252 A1 | 3/2021 | Hoffman et al. |
| 2021/0196318 A1 | 7/2021 | Kaufmann et al. |

FOREIGN PATENT DOCUMENTS

| | | |
|---|---|---|
| CN | 112074254 A | 12/2020 |
| CN | 115038398 A | 9/2022 |
| EP | 0634941 B1 | 7/1997 |
| EP | 2113283 A1 | 11/2009 |
| EP | 2615992 B1 | 7/2016 |
| EP | 1906858 B1 | 11/2016 |
| WO | 2010113072 | 10/2010 |
| WO | WO-2017048342 A1 | 3/2017 |
| WO | WO-2017177208 A1 | 10/2017 |
| WO | 2018152203 | 8/2018 |
| WO | WO-2018152203 A3 | 10/2018 |
| WO | WO-2019173107 A1 | 9/2019 |
| WO | WO-2021067463 A1 | 4/2021 |

OTHER PUBLICATIONS

"U.S. Appl. No. 16/486,030, Non Final Office Action mailed Sep. 8, 2020", 12 pgs.
"U.S. Appl. No. 16/486,030, Notice of Allowance mailed Dec. 24, 2020", 11 pgs.
"U.S. Appl. No. 16/486,030, Preliminary Amendment Filed Aug. 14, 2019", 10 pgs.
"U.S. Appl. No. 16/486,030, Response filed Aug. 10, 2020 to Restriction Requirement mailed Jun. 11, 2020", 8 pgs.
"U.S. Appl. No. 16/486,030, Response filed Dec. 8, 2020 to Non Final Office Action mailed Sep. 8, 2020", 12 pgs.
"U.S. Appl. No. 16/486,030, Restriction Requirement mailed Jun. 11, 2020", 7 pgs.
"U.S. Appl. No. 16/486,030, Supplemental Preliminary Amendment filed", 8 pgs.
"U.S. Appl. No. 16/926,335, Notice of Allowance mailed Nov. 9, 2020", 14 pgs.
"U.S. Appl. No. 16/926,335, Response filed Oct. 2, 2020 to Restriction Requirement mailed Aug. 4, 2020", 9 pgs.
"U.S. Appl. No. 16/926,335, Restriction Requirement mailed Aug. 4, 2020".
"U.S. Appl. No. 16/979,427 Preliminary Amendment filed Sep. 9, 2020", 10 pgs.
"U.S. Appl. No. 17/180,087, Preliminary Amendment filed Apr. 12, 2021", 7 pgs.
"Australian Application Serial No. 2019231573, First Examination Report mailed Feb. 8, 2021", 6 pgs.
"Australian Application Serial No. 2019231573, Response filed Apr. 27, 2021 to First Examination Report mailed Feb. 8, 2021", 40 pgs.
"Chinese Application Serial No. 201880011446.0, Voluntary Amendment filed Feb. 28, 2020", w/ English claims, 7 pgs.
"European Application Serial No. 18707575.9, Response to Communication Pursuant to Rules 161 and 162 filed Feb. 25, 2020", 23 pgs.
"European Application Serial No. 19710939.0, Response to Communication pursuant to Rules 161(1) and 162 EPC filed Apr. 15, 2021", 29 pgs.
"International Application Serial No. PCT/US2018/018182, International Preliminary Report on Patentability mailed Aug. 29, 2019", 14 pgs.
"International Application Serial No. PCT/US2018/018182, International Search Report mailed Sep. 10, 2018", 7 pgs.
"International Application Serial No. PCT/US2018/018182, Invitation to Pay Add'l Fees and Partial Search Report mailed May 23, 2018", 15 pgs.
"International Application Serial No. PCT/US2018/018182, Written Opinion mailed Sep. 10, 2018", 12 pgs.
"International Application Serial No. PCT/US2019/020130, International Preliminary Report on Patentability mailed Sep. 24, 2020", 7 pgs.

(56) References Cited

OTHER PUBLICATIONS

"International Application Serial No. PCT/US2019/020130, International Search Report mailed Jun. 12, 2019", 7 pgs.
"International Application Serial No. PCT/US2019/020130, Written Opinion mailed Jun. 12, 2019", 10 pgs.
Campbell, Luke, et al., "Intraoperative Real-time Cochlear Response Telemetry Predicts Hearing Preservation in Cochlear Implantation", Otology & Neurotology; vol. 37(4), (Apr. 2016), 10 pgs.
Dahm, MC, et al., "The postnatal growth of the temporal bone and its implications for cochlear implantation in children", Acta Otolaryngol Suppl. 505., (1993), 4-39.
Desrosiers, M, et al., "Precise vocal cord medialization using an adjustable laryngeal implant: a preliminary study", Otolaryngol Head Neck Sur, 109(6), (1993), 1014-1019.
Fasano, Alfonso, et al., "MDS SIC Blog: Recent Advances in Deep Brain Stimulation (DBS) Technology", International Parkinson and Movement Disorder Society, [Online]. Retrieved from the Internet: <URL: https://www.movementdisorders.org/MDS/Scientific-Issues-Committee-Blog/Recent-Advances-in-DBS-Technology.htm>, (Mar. 2018), 3 pgs.
Gantz, Bruce J., et al., "Hybrid 10 Clinical Trial", Audiol Neurotol 2009;14(suppl 1):DOI: 10.1159/000206493, (2009), 7 pgs.
Greene, Nathaniel, et al., "Intracochlear pressure transients during cochlear implant electrode insertion", Otol Neurotol. 37(10), (2016), 1541-1548.
Jurawitz, Marie-Charlot, et al., "Hearing Preservation Outcomes with Different Cochlear Implant Electrodes: Nucleus® Hybrid TM-L24 and Nucleus Freedom Tm CI422", Audiol Neurotol 2014;19: 293-309; DOI: 10.1159/000360601, (2014), 17 pgs.
Mittmann, Phillipp, et al., "Intracochlear Pressure Changes due to 2 Electrode Types: An Artificial Model Experiment", Otolaryngology—Head and Neck Surgery, vol. 156(4), (Dec. 2016), 712-716.
Montgomery, William, et al., "Montgomery Thyroplasty Implant for vocal fold immobility: phonatory outcomes", Ann Otol Rhinol Laryngol, 109(4), (2000), 393-400.

Mowry, Sarah E., et al., "New Frontiers in Cochlear Implantation: Acoustic Plus Electric Hearing, Hearing Preservation, and More", Otolaryngologic Clinics of North America. vol. 45, Issue 1., (2012), 187-203.
Woodson, Erika A., et al., "The Hybrid Cochlear Implant: A Review", Cochlear Implants and Hearing Preservation. Adv Otorhinolaryngol. Basel, Karger, 2010, vol. 67., (2010), 125-134.
U.S. Appl. No. 16/926,335 U.S. Pat. No. 10,945,761, filed Jul. 10, 2020, Modular Implant Delivery and Positioning System.
U.S. Appl. No. 17/180,087, filed Feb. 19, 2021, Modular Implant Delivery and Positioning System.
"Chinese Application Serial No. 202080076185.8, Notification to Make Rectification mailed May 24, 2022", with machine translation, 2 pgs.
"International Application Serial No. PCT/US2020/053579, International Preliminary Report on Patentability mailed Apr. 14, 2022", 10 pgs.
"International Application Serial No. PCT US2020 053579, International Search Report mailed Jan. 18, 2021", 3 pgs.
"International Application Serial No. PCT US2020 053579, Written Opinion mailed Jan. 18, 2021", 8 pgs.
"Australian Application Serial No. 2020357745, First Examination Report mailed Mar. 16, 2023", 4 pgs.
"Australian Application Serial No. 2020357745, Response filed Jun. 13, 2023 to First Examination Report mailed Mar. 16, 2023", 74 pgs.
"Australian Application Serial No. 2020357745, Subsequent Examiners Report mailed Jul. 13, 2023", 3 pgs.
"Australian Application Serial No. 2020357745, Response filed Oct. 10, 2023 to Subsequent Examiners Report mailed Jul. 13, 2023", 3 pgs.
"European Application Serial No. 20870940.2, Extended European Search Report mailed Feb. 2, 2024", 10 pgs.
"U.S. Appl. No. 17/180,087, Notice of Allowance mailed Mar. 14, 2024", 14 pgs.

\* cited by examiner

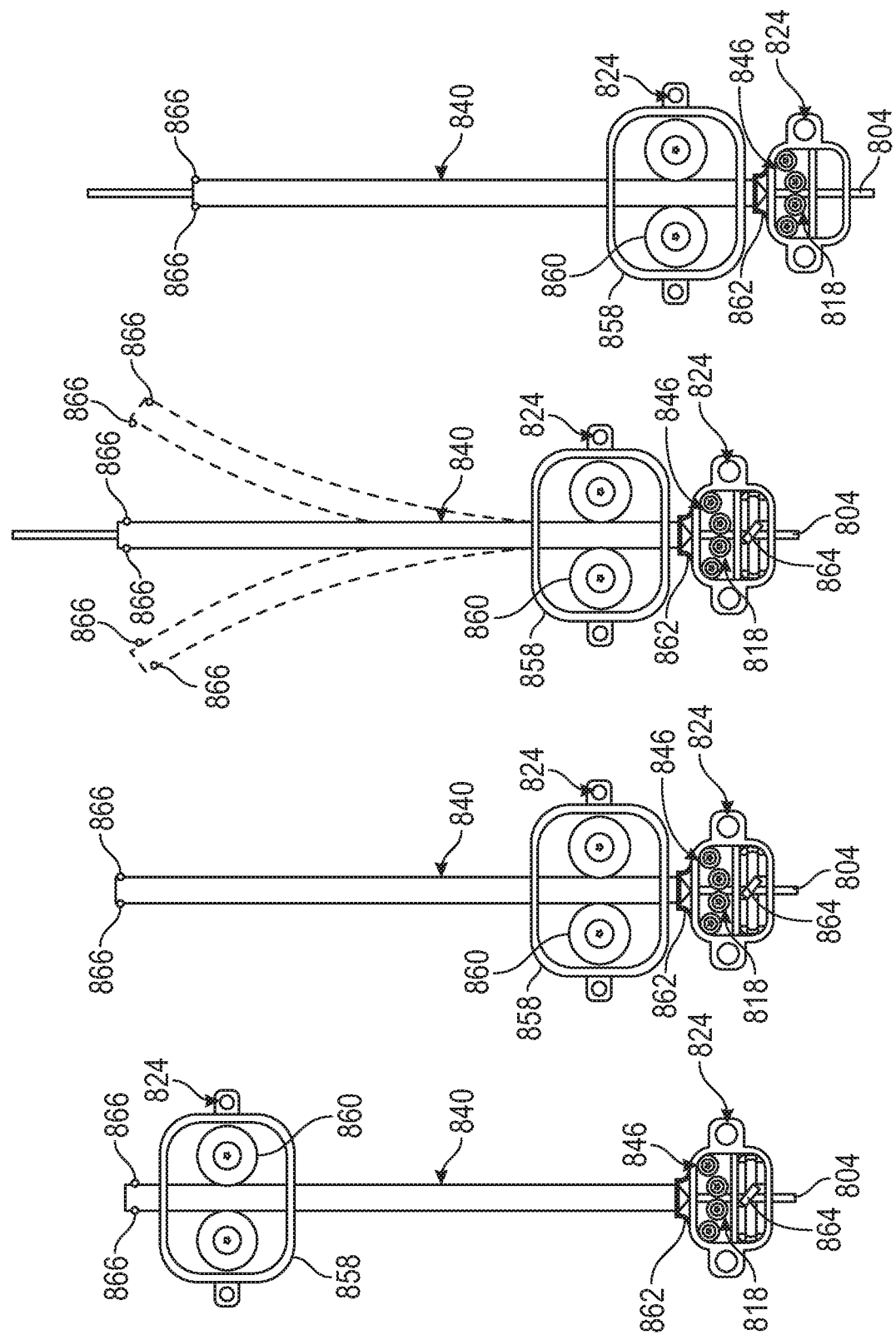

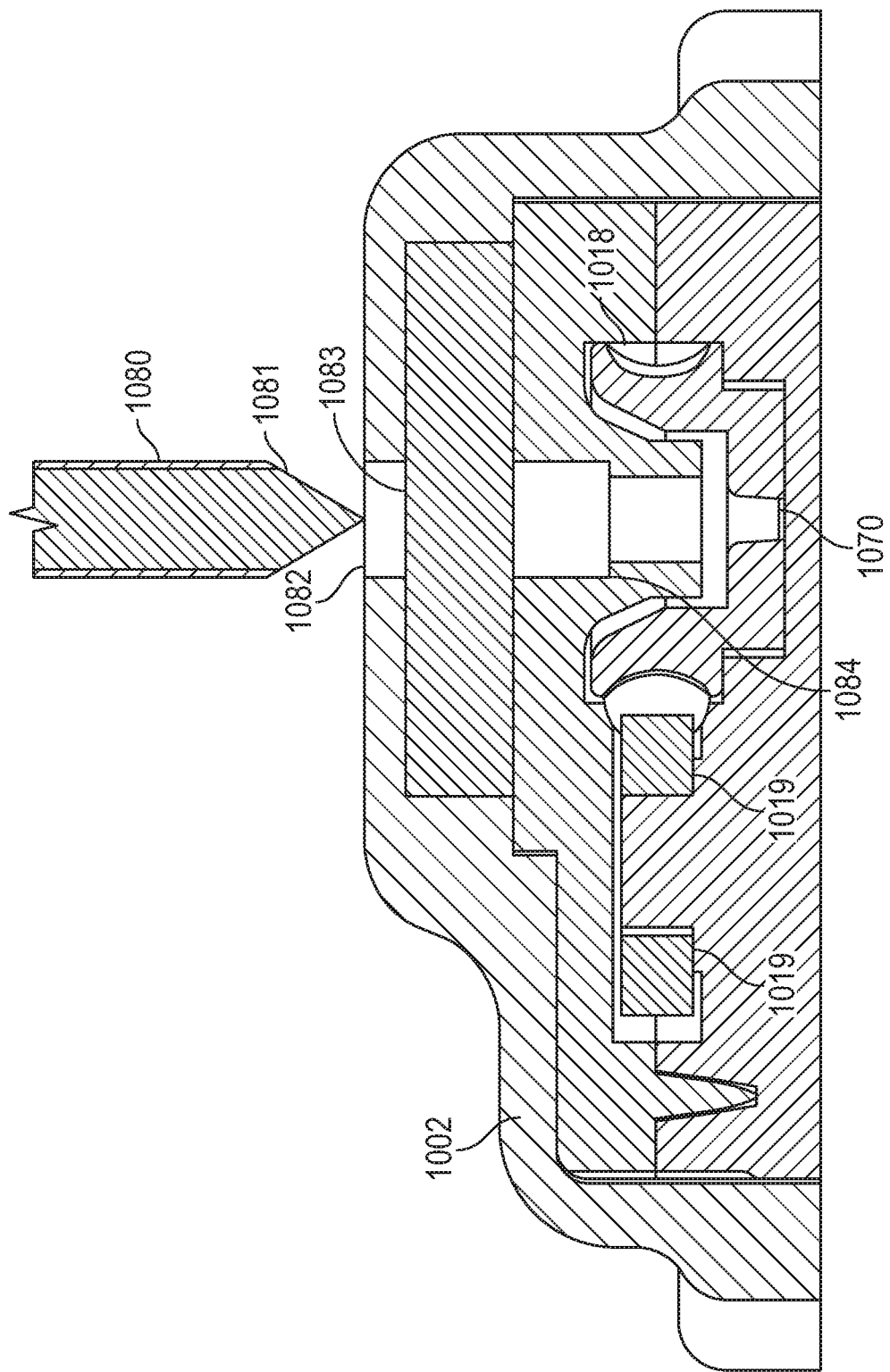

MODULAR IMPLANT DELIVERY AND POSITIONING SYSTEM

PRIORITY AND RELATED APPLICATIONS

This application claims the benefit of priority to Kaufmann et al., U.S. Provisional Patent Application No. 62/908,505, titled, MODULAR IMPLANT DELIVERY AND POSITIONING SYSTEM, filed Sep. 30, 2019, and is hereby incorporated by reference herein in its entirety.

TECHNICAL FIELD

This document relates generally to medical systems and more particularly to systems, devices, and methods for robotic control of delivery, positioning, and manipulation of an implant, such as a neuromodulation electrode in the spine or brain. Neuromodulation devices can include spinal cord stimulators, deep brain stimulators, cranial nerve stimulators, renal nerve stimulators, motor nerve stimulators, sacral nerve stimulators, or peripheral nerve stimulators.

OVERVIEW

Spinal cord stimulation—Chronic neuropathic pain is the pain caused by a lesion or disorder of the somatosensory nervous system as defined by the International Association for the Study of Pain. Neuropathic pain affects 7-10% of the general population. Neuropathic pain encompasses many conditions including neuropathies, damage to peripheral nerves or spinal nerve roots, deafferentation pain, central pain following stroke or spinal cord injury, failed back surgery syndrome (FBSS), and complex regional pain syndrome. Neuropathic pain can have detrimental impact on quality of life, sleep, anxiety, and depression. A spinal cord stimulator (SCS) has proven to be a better solution than treatments with pharmaceuticals or opioids to managing neuropathic pain condition and is considered the gold standard treatment.

The SCS treatment consists of one or more electrical leads or paddles surgically implanted in the epidural space of the spinal canal, connected to an implantable pulse generator. Each lead or paddle has several electrical contacts capable of delivering a weak electrical current to the spinal cord or target site, evoking a feeling of peripheral paresthesia or anesthesia.

Implanted electrode paddles are more invasive requiring open laminectomy approach under general anesthesia. Whereas implanted elongated leads are manually inserted with minimally invasive approach by a surgeon under live fluoroscopy into the epidural space of the spinal canal. Leads are positioned manually by the surgeon to provide the highest probability of paresthesia coverage. Patients often undergo local anesthesia and can verbally confirm full-paresthesia coverage, thus confirming proper electrode positioning.

A major complication in SCS surgery is from hardware-related complications. Hardware complications can include lead migration, lead connection failure, and lead breakage. SCS complications have been reported at 30 to 40% in multiple studies. Once the neurostimulation system is implanted, movement of the lead within the epidural space may occur. These events may result in uncomfortable stimulation or loss of therapy requiring reprogramming, surgical replacement of the leads, or repeat corrective surgery. Despite initial stimulation lead being properly positioned during initial surgery, another loss of SCS efficacy over time can occur due to the formation of scar tissue around the leads. Revision surgeries may be required to adjust the lead position or replace the lead in order for increased clinical efficacy to be obtained. The present invention can prevent revision surgeries by providing a means to remotely or percutaneously adjust the lead position and stimulation location over time to account for changing physiologic conditions or lead migration.

Additionally, traditional manual placement of the electrode array leads provides an opportunity for inter-operator variability among surgeons, with resulting variability in patients' outcomes. Manual insertion of the leads into the epidural space can cause insertion trauma which can induce scar tissue formation and decreased stimulation treatment efficacy. Precise and controlled placement of electrode array decreases variability between surgeon insertion techniques and improves electrode array positional accuracy with fewer side effects. Using the present invention, robotic-assisted precision placement of an electrode array enables targeted stimulation for improved paresthesia effect to only the area that needs pain relief. Enhanced placement precision decreases the adverse side effects of undesirable stimulation such as groin or foot pain, common in current procedures.

The individual electrode contacts on current electrode array leads may be circumferential bands or partial paddles. Banded or non-directed electrode contacts may induce larger stimulation fields and increased chances of stimulating target as with less directed field focus. Alternatively, paddle or partial electrode contacts have the benefit of more directed electrical stimulation field but require a more precise placement at target lesion for efficacy or larger number of contacts per individual array lead. Similarly, partial banded or paddle electrode array placement requires proper rotational orientation of the individual leads to effectively direct the electric stimulation field. Partial banded electrode arrays require lower stimulation power for paresthesia control compared to complete banded electrode contacts. Incorrect orientation of the electrode contacts requires more electric power to obtain adequate paresthesia coverage. In order to decrease electrical power and direct electrical stimulation field for partial banded electrode contacts, rotational control of the electrode array is required. As in deep brain stimulation, current circumferential lead contacts can be adjusted by stimulation software parameters to create directional electrical stimulation.

The present inventors have recognized a need to provide precise and dynamic positioning of an elongate member that can include a sheath, an electrode, an half or partial banded electrode array, or a sheath and an electrode or electrode array, for the purpose of decreasing adverse events and side effects. In certain examples, an elongate member can be physically rotated and precisely positioned remotely or minimally invasively to physically direct the stimulation field. This may enable creation of smaller, less traumatic stimulation leads which do not require as many electrode contacts and current carrying wire. Similarly, high impedance tissues or regions around the electrode array can lead to unintended or inadequate stimulation. With present invention, the elongate member may be protected from or rotated and steered away from areas of high impedance tissue for improved stimulation efficacy and patient outcomes.

Deep Brain Stimulation Overview and Directed Array Positioning—A deep brain stimulator is another neurostimulator type used to treat movement disorders and modulate behavior. Current deep brain stimulation leads are linear arrays inserted in linear superficial to deep trajectories with a cylindrical field emitting from the rod-shaped electrode array. However, a specific target site, lesion, or neural track may be a complex architecture or path in multiple spatial dimensions. The ideal stimulation field geometry would follow these neurological paths for optimal efficacy. As such there is a need to physically manipulate the electrode array and contacts into various complex paths or stimulation field architectures. This can be achieved with current invention which enables a bendable and steerable electrode array deformable in complex geometries to further tailor stimulation efficacy in multiple degrees of freedom and planes.

Current electrode arrays are limited by their span depending on array shape and size (see image of commercially available leads below). While current arrays have numerous electrode contacts in a linear elongated superior-inferior span, these are limited in their ability to position contacts in the medial-lateral spans without inserting multiple lead arrays. Alternatively, smaller arrays are less traumatic to insert but require more precise placement for optimal target stimulation, Therefore, the ability to more precisely position and manipulate the electrode array position in both the rostral-caudal, anterior-posterior, and importantly medial-lateral spans would improve stimulation pain targeting, focus the stimulation field, decrease implanted lead number/size, and decrease unwanted paresthesia or side effects.

After initial neurostimulator implantation and placement, physiologic movement or pain patterns change. Altering the initial electrode array contact locations to adapt and adjust to the changing pain patterns traditionally requires a revision surgery to reposition or remove and reinsert into a new location. The present invention described enables the ability to manipulate the electrode lead physical position to improve device efficacy and patient treatment outcomes without revision surgery.

The present invention improves patient outcome with neurostimulators through robotically-controlled neuromodulation and steerable initial placement of electrode arrays for precise and atraumatic implant delivery, plus the ability to non- or minimally invasively reposition a physical electrode array location to adapt to evolving physiological patterns.

Sensing and Adaptive Surgical Assistance System—The present subject matter relates to surgical insertion system to provide surgeons with a precise and controlled insertion and positioning procedure. This device establishes a foundation to further improve the surgical experience with the integration of a suite of technologies within the operating room. Real-time feedback enables the robotics platform to dynamically sense and respond to real-time physiological changes. Currently, surgeons must draw from a variety of fragmented systems and adjust their procedure manually. As the number of useful technologies increases, simultaneous interpretation of information from all these systems will become exponentially more difficult and not feasible to interpret and respond to manually by the surgeon. In certain examples, a robotic surgical platform can address this multitude of information and information sources by bringing it all to a single, modular platform which senses, interprets, and assists with appropriate responses and surgical decisions.

The technology works through a central processing system, which takes the output of proprietary algorithms and updates the insertion control parameters of a robotic insertion system. These real-time inputs come from three major systems: Optical Visualization, Radiographical Tracking, and Electrophysiological Monitoring.

Optical Visualization consists of cameras facing the surgical site and surgeon. These cameras will then detect key objects in the field of view and create a three-dimensional map of the visible anatomy as well as surgeon and device movements. Custom logic will identify the state of procedure data, such as the angle of insertion, speed, acceleration, and potential undesirable actions (i.e. electrode buckling or lead migration).

Radiographical tracking provides non-visible feature insights. By utilizing trackers that show up in imaging systems such as fluoroscopy, MRI and CT, the system can map pre-operative patient-specific imaging with live surgical progress. The system algorithms can then use this information to make adaptations based on the state of the system and patient functional structures.

Electrophysiological monitoring allows for system adaptability to cellular signatures that can be indicative of patients' health or local site and cellular health. Electrical signals are able to be picked up within the body, which can be fed to algorithms for adjusting the surgery accordingly, or warning the user of harmful changes.

Surgical Insertion Vision and Control System—The system design shown (see FIG. 16) gives a visual representation of the logical components of the feedback and control system. These components are intended to add benefit by considering patient anatomy, ongoing markers/input indicating state of the system and patient, and easy to use interface elements. The Central Processing & Control System (1601) is the component that ties inputs from storage media and control devices (i.e. foot pedal, touchpad, etc.) with outputs of the feedback algorithms (1630) and turns it into meaningful parameters for adjusting the insertion device during a procedure. Those parameters are values that affect things like position of the sheath or adjustable lead, speed of insertion, acceleration, and insertion angles.

The Real-Time Procedure Feedback section provides the components about how certain surgical variables can be processed to automatically adjust, or suggest adjustment, of the insertion parameters. The first main feedback source is the Image Processing System (FIG. 16, 1631)—this is a combination of optical cameras that can detect objects such as the implant, insertion device, and relevant surgical tools. There are two cameras identified in the system so that they can provide stereoscopic mapping of the surgical site, which essentially means it has three-dimensional (3D) capabilities. 3D information is key in situations where calculating distances and creating a point cloud may be useful in controlling insertion or repositioning. The Signal Processing System (FIG. 16, 1634) takes input from an analog electrophysiological sensor and provides filtering, amplification, analog-to-digital conversion, and other standard signal-processing activities. This system is useful to record and observe physiological changes in the patient throughout the procedure, which can be indicative of successful outcomes in surgery. The Patient Monitoring System (FIG. 16, 1636) provides the means to capture other relevant data from the operating room. This may take input from operating room peripherals and environment monitoring sensors such as a monocular camera observing relevant objects in the room, microphones capturing sound data input from the user or patient or other surgical systems, temperature sensors, or patient-system-interaction devices.

The Peripherals Management System (FIG. 16, 1610) is the hub that handles all other devices that are connected directly or indirectly to the system. Human Interaction Devices (FIG. 16, 1613) such as a mouse, keyboard, touchpad, foot pedal, joystick, etc. are attached and handled here. Patient Pre-Op Imaging storage devices (i.e. USB stick), or imaging database servers (i.e. Cloud storage) (FIG. 16, 1612) are attached here to load relevant input data. The Central Processing and Control System & Graphical User Interface are subsequently updated to display this information in a useful, simple way. Similarly, the Live Patient imaging System (FIG. 16, 1611) is a device or system that provides Fluoroscopy/CT/MRI input during the procedure—which then updates elements in the user interface and can be fed into the Algorithm Processing & Detection System to automatically adjust the insertion device.

In certain examples, the modular design of the robotically assisted implantation system, as discussed in this document, allows for easy replacement or interchange of a particular module. This may not only improve the system reusability and efficiency but may also reduce the cost of system maintenance. For example, the external positioning unit may be a single-use device positioned in a sterile surgical field or in contact with the patient during an implantation surgery and is disposable after surgery. The computerized control unit may be positioned in a non-sterile field, such as a control room, and can be reused with interchangeable external positioning units.

The external positioning unit can be a non-implanted external device. Compared to a partially or completely implantable insertion device, the external positioning unit discussed herein may substantially reduce the risk of complications associated with surgical implantation, extraction, or replacement of otherwise partially or completely implantable insertion device. The external positioning unit also has the advantage of easy trouble-shooting, maintenance, and replacement, thereby reducing cost of the system and the procedure. As to be discussed in the following, the external positioning unit may have a small size with limited mechanical and electrical parts, thus making it flexible for external fixation to a patient.

Although the discussion in this document focuses on a neuromodulation implant, this is meant only by way of example and not limitation. It is within the contemplation of the present inventors, and within the scope of this document, that the systems, devices, and methods discussed herein may be configured for robotically delivering, steering, positioning, or extracting various types of implants or prosthesis. By way of non-limiting examples, the implants may include leads, catheter, guidewire, or other mechanical or electrical devices. The implants may be designed for temporary or permanent implantation. The implants may be used for medical diagnosis of a disease or other conditions such as diagnostic catheters, or for therapeutic purposes of cure, mitigation, treatment, or prevention of disease, such as implantable electrodes for stimulating cardiac, neural, muscular, or other tissues. In addition to new implantation, the systems, devices, and methods discussed herein may also be used to surgically reposition or replace an existing implant.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 8A-8D illustrates generally various states of a modular sheath and electrode positioning device in accordance with the present subject matter.

FIGS. 10A-10D illustrate generally creation and use of a mechanical percutaneous implant connection port, in accordance with an example embodiment of the present disclosure.

DETAILED DESCRIPTION

Figure 1:
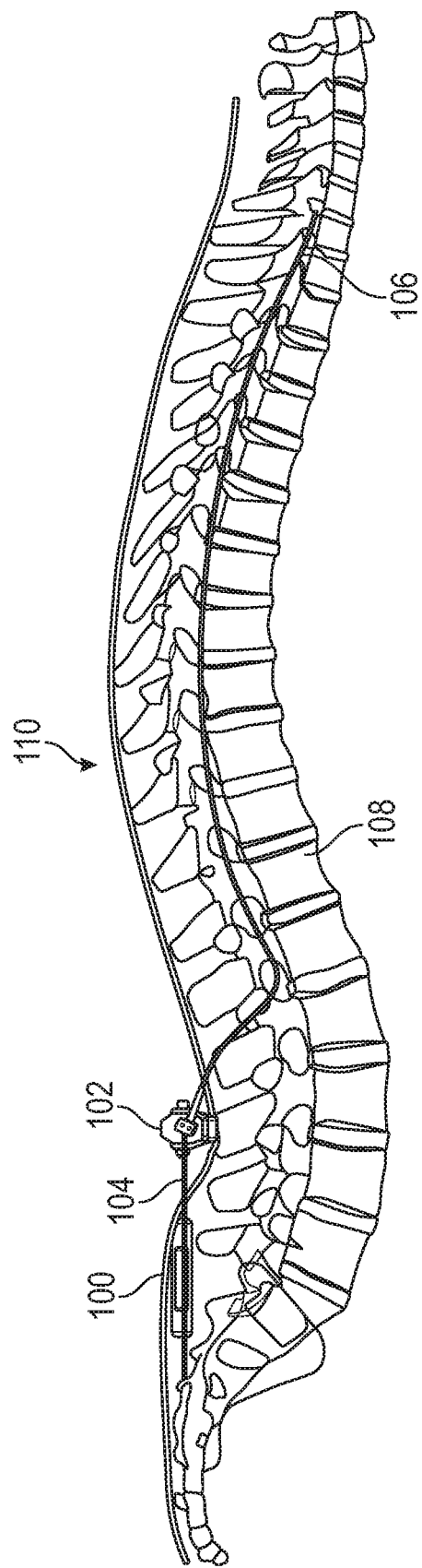
FIG. 1 is a side view elevation of an external positioning device, in accordance with an example embodiment of the present disclosure.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Disclosed herein are systems, devices, and methods for robotically assisted implantation of an implant in a patient. Examples of the implants may include leads, catheter, guidewire, guide sheath, or other mechanical or electrical devices. The implants may be designed for temporary or permanent implantation. The implants may additionally be used for medical diagnosis of a disease or other conditions such as diagnostic catheters, or for therapeutic purposes of cure, mitigation, treatment, or prevention of disease, such as implantable electrodes for stimulating cardiac, neural, muscular, or other tissues. The present system may be implemented using a combination of hardware and software designed to provide precise control of implant movement, such as insertion of a neuromodulation implant during a spinal cord stimulation implantation surgery or a deep brain stimulator and/or directed array positioning surgical procedure. The system includes an implant-positioning unit a control console communicatively coupled to the implant-positioning unit. The implant-positioning unit includes a drive head configured to engage an elongate member of the implant and robotically deliver and position the implant into a target implantation site. The control console may have a user interface that enables a user to input motion control instructions. The control console may generate a motion control signal, according to a specific motion control instruction, to control the external positioning unit to propel the implant into a target implant site.

The device can move/position one or multiple SCS implant electrodes, or cochlear implant electrodes, or neural implant electrodes, neuromodulators or signal processing electrodes, or catheters, or cameras, or clamps, or cautery tools, or biopsy tools, or surgical tools, drug delivery catheters or a combination of these. In some examples, the operation and design of the insertion control unit is similar to the devices described in commonly assigned U.S. Patent Application No. PCT/US2018/018182 entitled "MODULAR IMPLANT DELIVERY AND POSITIONING SYSTEM," which refers to wheel arrangement to engage elongate members of an implant, the description of which is incorporated herein by reference in its entirety. Further, other aspects of the system discussed herein includes design and operation similarities with devices and systems discussed in commonly assigned U.S. Provisional Patent Application No. 62/872,625 entitled "MODULAR IMPLANT DELIVERY AND POSITIONING SYSTEM," which refers to a modular implant delivery mechanism, the description of which is incorporated herein by reference in its entirety.

The system consists of modular housings that can be permanently implanted or removed after positioning. The housing can have an entrance for the implant/tool to be positioned to enter. And an exit for the implant/tool to be positioned to exit. The entrance and exit can be sealed by a valve, clamp, or electrical feedthrough. The housing can have fixation flanges (screw/suture fixation points). The device can be fixated in place by screws, or sutures, or bone paste, or osteointegration, or clamps or other implant fixation methods.

The housing can include one or more drive wheels. Drive wheels can turn and move linearly. Turning the drive wheels drives the implant/tool forwards and backwards. Linearly moving the drive wheels turns/spins the implant.

Connected to the housing is a sheath or sheaths to guide and or protect the stimulating electrode. The sheath can be composed of a stiff or flexible material or a combination such as a stay put or gooseneck sheath. The sheath can be permanently deformed and stays put when placed. The housing contains an array (1 or more) actuators capable of steering the sheath. The sheath will be fully or partially steerable to desired shape or path.

Steering of the sheath can be controlled mechanically by pull cords/tendons in the sheath wall connected to distal pull rings, or pneumatically controlled with fluids in the sheath wall, or electrically controlled with wires and actuators in the sheath wall, or magnetically with magnets in the sheath wall, or any combination of these. Steering can be controlled percutaneously with removable disposable actuators that engage the housing actuator array, or transcutaneous with a wireless power supply and control and actuating electronics implanted, or magnetically with removable disposable magnets, or by pneumatics with disposable removable pumps. Actuators, disposable or permanently implantable, can be piezo electric in nature, or mechanical in nature, or magnetic in nature, electromechanical or pneumatic in nature. Steering can be multiple degrees of freedom unidirectional, bidirectional, or omnidirectional. Positioning of the implant/tool can involve compound curve or out of plane curves of the steerable sheath.

Position and velocity are controlled with feedback. Position and velocity feedback are obtained with physical sensing of the actuators with hall sensors, or strain sensors, or magnetic sensors, or resistive sensors or a combination of these sensors. Or feedback can be obtained with bio signal processing. The steerable sheath can consist of a flexible tube in the implantable version, or half tube or slit tubes in the removable disposable embodiments. A fully implantable sheath can be completely sealed at the tip and the lead moved within preventing scar tissue build that can limit adjustment movements.

FIG. 1 is a side view elevation of an example external, non-implantable spinal cord stimulator, implant-controlled insertion system including an external positioning device 102, in accordance with an example embodiment of the present disclosure. The external positioning device 102, or steering device, is shown mounted to a patient whose anatomy can be identified by a spine 108 and skin 110. The system can include a stimulator processor circuit 100, an electrode 104 with an electrode tip 106, and the positioning device 102. The positioning device 102 can robotically control an attached drive head, or drive wheel assembly, to an optimal angle and orientation of insertion and can control insertion speed of the electrode 104 and positioning of the electrode tip 106 with feedback from stereoscopic cameras, position sensors, pre-op patient imaging analysis, patient biometric sensors and or surgeon input feedback. The drive head of positioning device 102 can dip onto the electrode 104, or electrode array and can use drive wheels to insert or retract the electrode tip 106.

Figure 2:
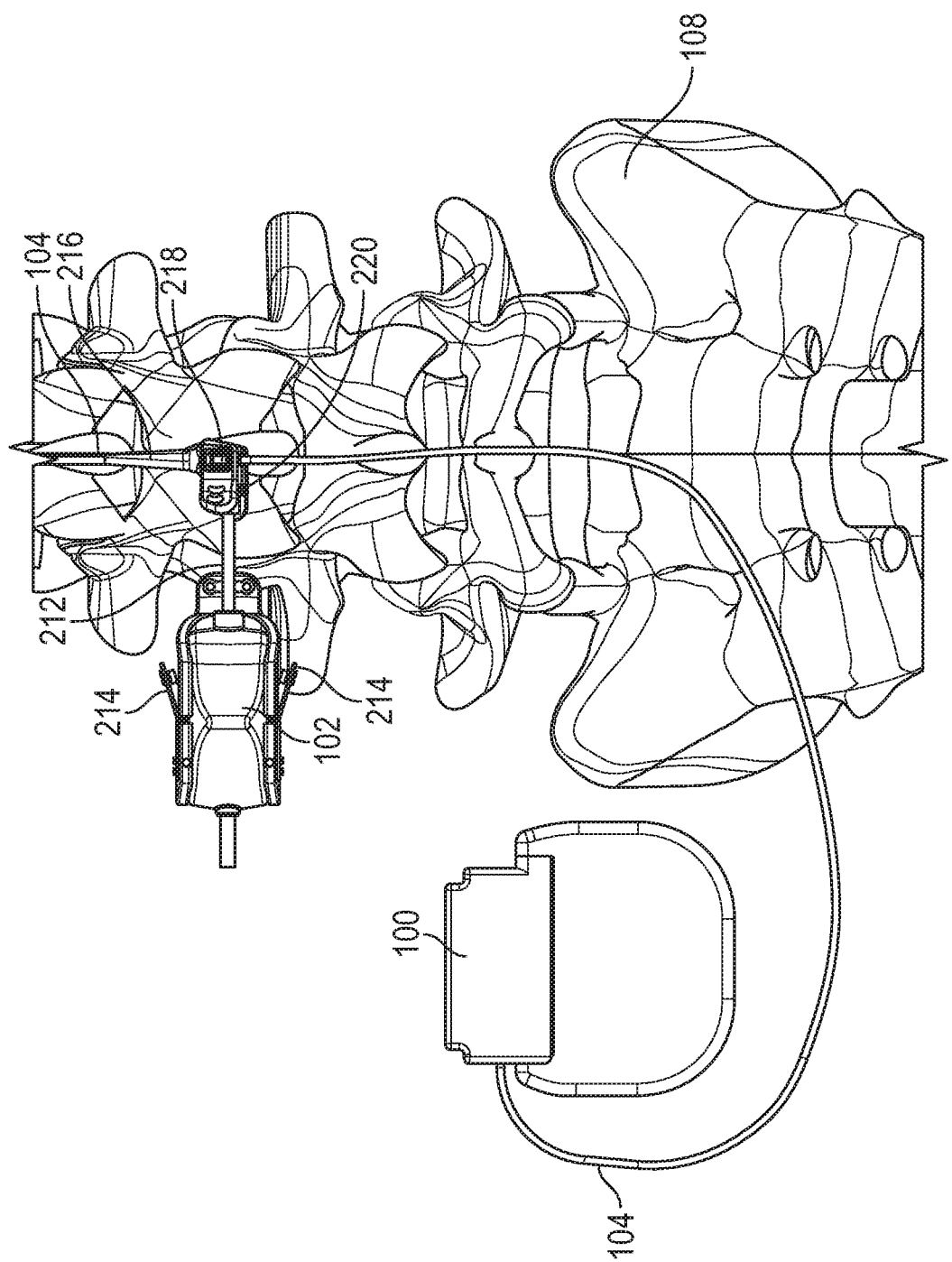
FIG. 2 is a top view elevation of an external positioning device, in accordance with an example embodiment of the present disclosure.

FIG. 2 is a top view elevation of an external positioning device 102, in accordance with an example embodiment of the present disclosure, in certain examples, the insertion device can be mounted to the patient via a sliding mount 214 and can connect to a drive head 220 via an adjustable neck 212. As discussed above the drive head can clip to the electrode and drive wheels of the drive head can move the electrode 104 for insertion, retraction or positioning of the electrode tip within or near the spinal column of the patient. Split guide tips 216 may enter the patient through soft tissue and clamp open for removal leaving implant lead in place after securing.

Figure 3:
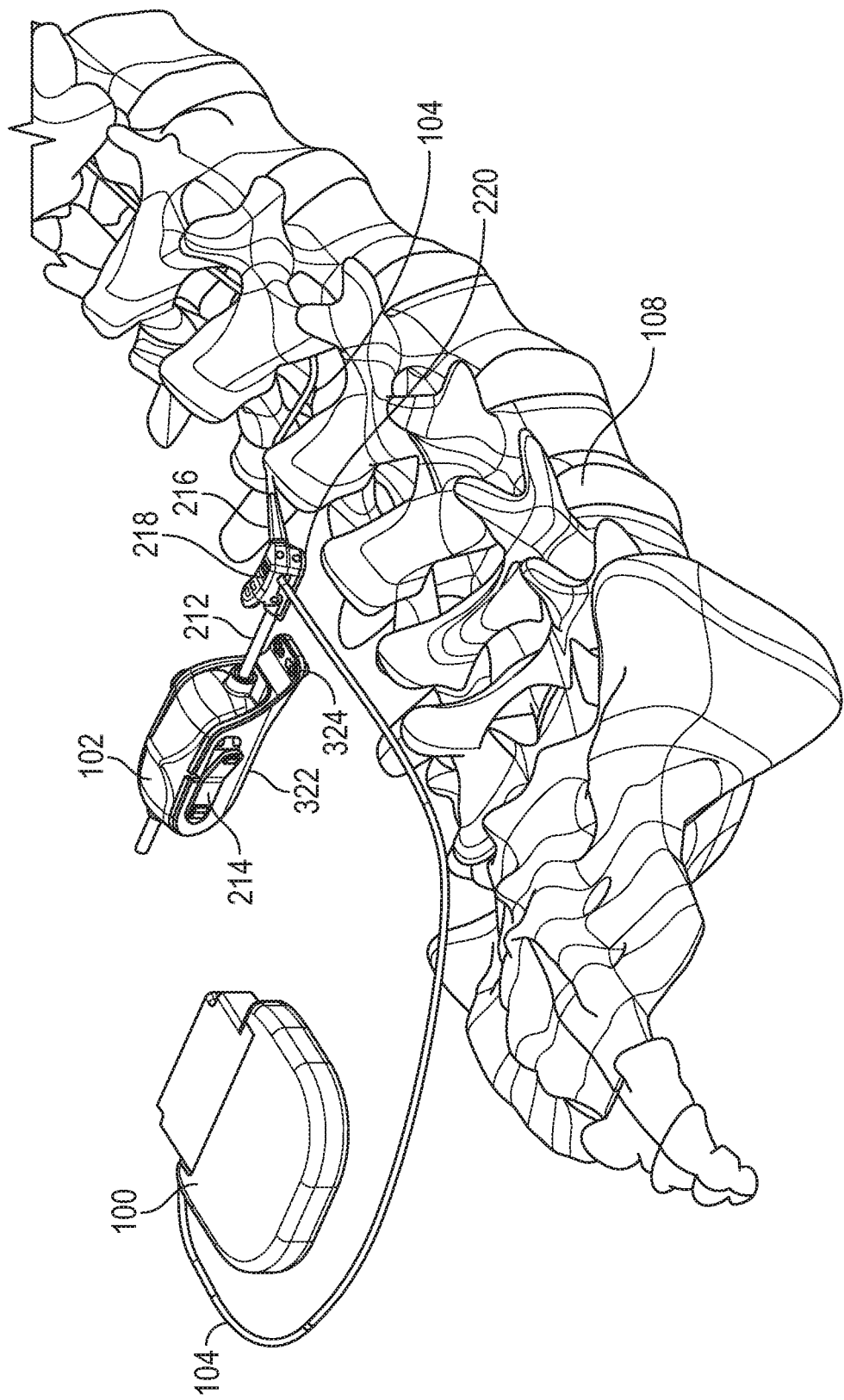
FIG. 3 is a prospective view of the external positioning device, in accordance with an example embodiment of the present disclosure.

FIG. 3 is a prospective view of the external positioning device 102, in accordance with an example embodiment of the present disclosure, in certain examples, the sliding mount 214 can be equipped with screw/suture points to fix the siding mount and the positioning device 102 to the patient, such as to vertebra, providing stability during an insertion or positioning procedure. In certain examples, the positioning device 102 can be locked in place by position locking toggles of the sliding mount 214 for added stability. Once the positioning device 102 is positioned, the drive head 220 can engage with or can clip around an elongate member, a spinal cord stimulator electrode 104, and can provide the motion and control insertion into the epidural space of the spinal canal by extruding the lead through drive wheels. In certain examples, the drive wheels 218 may include a single driven wheel and an idler wheel. The positioning device 102, sometimes referred to as an external control unit, can robotically slide along the sliding mount and position the drive head via the adjustable neck 212 in a range of orientations using feedback from stereoscopic cameras, sensors, pre op patient imaging analysis, patient biometric sensors and surgeon input. Once a desired target area has been reached by the stimulating tip, or electrode tip (FIG. 1, 106), of the electrode lead 104, the drive head 220, and positioning device 102, can be unclipped or disengaged from the electrode lead 104 and removed. Split guide tips 216 may enter the patient through soft tissue and clamp open for removal leaving implant lead in place after securing. In certain examples, the positioning device 102 and drive head 220 can be disposed of following a insertion or repositioning procedure.

Figure 4:
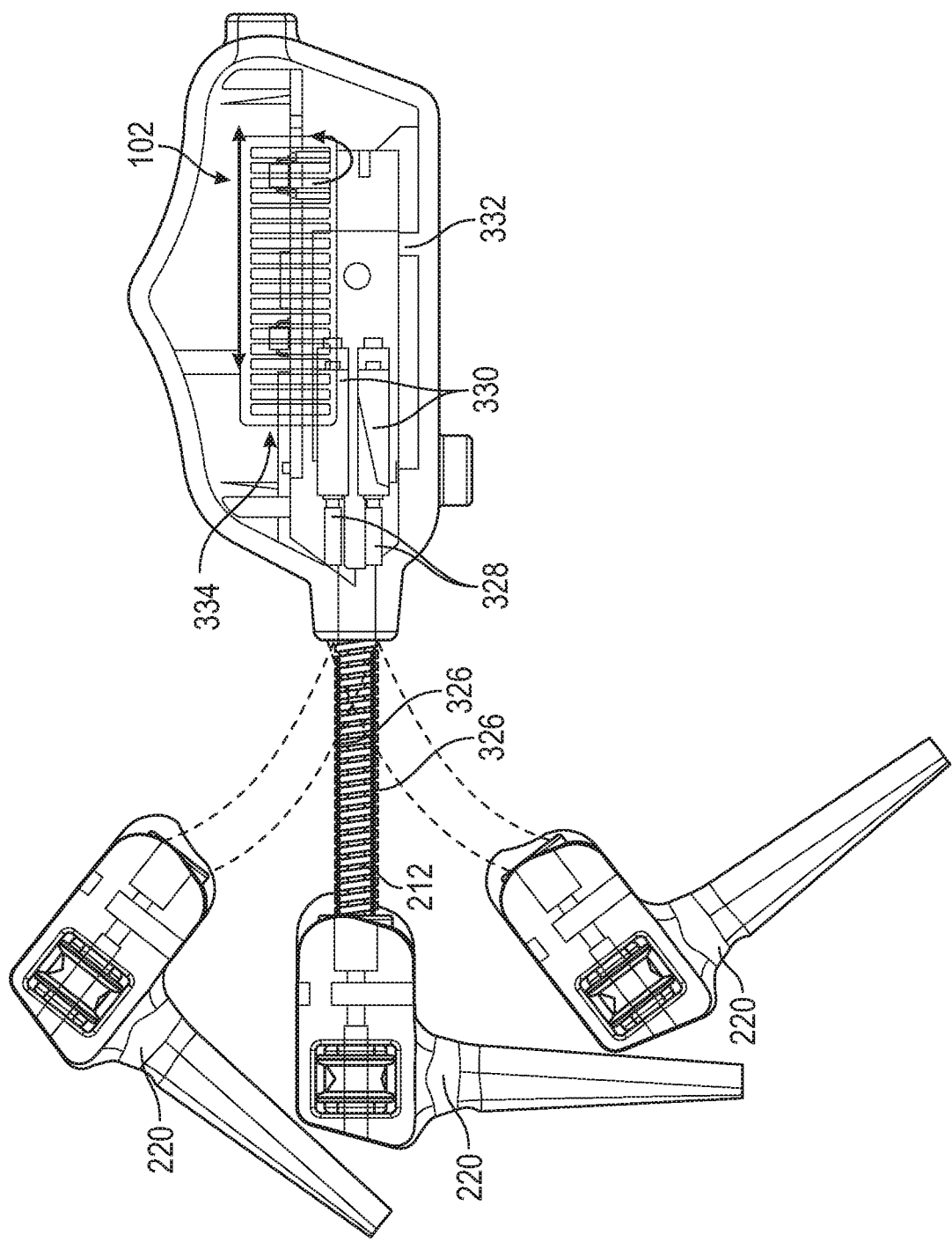
FIG. 4 illustrates generally an example of the range of adjustment of a robotic drive head positioning mechanism of a positioning device in accordance with an example embodiment of the present disclosure.

FIG. 4 illustrates generally an example of the range of adjustment of a robotic drive head 220 positioning mechanism of a positioning device 102, in accordance with an example embodiment of the present disclosure. The positioning device 220 can include electronics such as control circuitry and batteries, a drive motor 332 for providing electromotive force and driving the drive wheels of the drive head 220, one or more pull wire mandrels 328, and one or more pull wire mandrel motors 330. The pull wire mandrels 328, via the corresponding motors 330, can retract and release pull wires 326 that extend with the adjustable neck 212 and can bend the adjustable neck 212 not only in the plane illustrated by FIG. 4 but in other planes or directions as well. The enclosure of the positioning device can robotically move and rotate within the sliding mount allowing for any angle of insertion in multiple degrees of freedom and planes. Manual positioning is also possible with feedback to monitor and control the system through sensors. In an example, a combination of optical (stereotactic imaging) as well as motor positioning feedback (e.g., magnetic) can be used to control motors 330, 332 of the positioning device 102.

Figure 5:
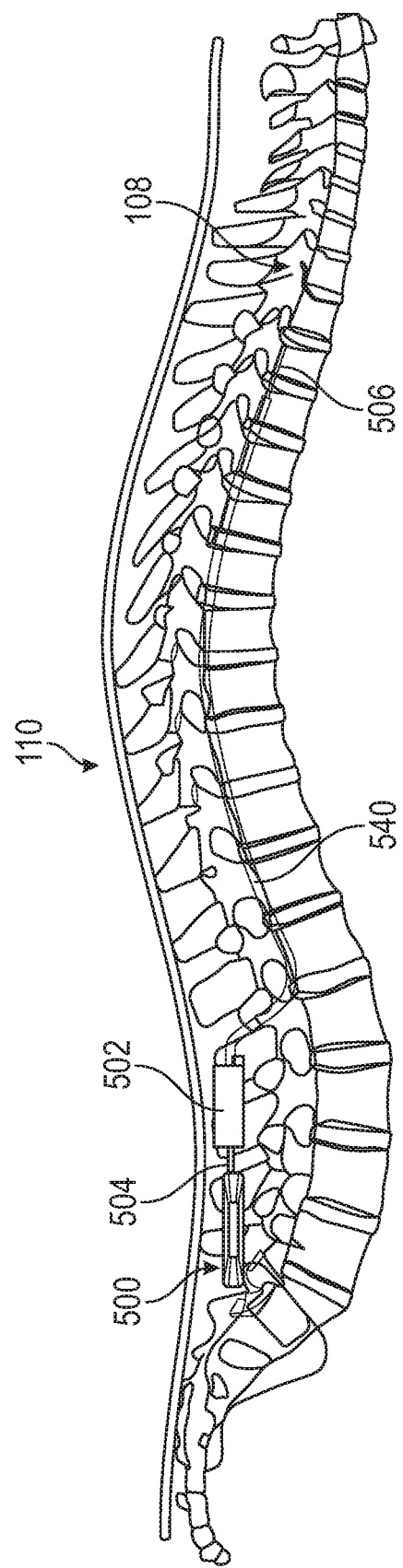
FIG. 5 illustrates generally an example implant positioning device 502.

FIG. 5 illustrates generally an example implant positioning device 502. The implant positioning device 502, or steering device, or implant, is illustrated implanted in a patient under the skin 110 and within or near the spine 108. In other examples, the implant position device 502 can be implanted on the skull for positioning electrode within the brain. The implant positioning device 502 is part of a system that can include a stimulator 500, electrode 504 and electrode tip 506, and an adjustable sheath 540. In certain examples, the implant positioning device 502 can allow post-operative adjustments of the position of the sheath 540 and stimulating electrode tip 506 percutaneous mechanically via implant connection ports, transcutaneous electrically via wireless near-field communication (NFC), or combination thereof. When implanted, the positioning device 102 can be secured to soft tissue or bone using screw/suture points. The positioning device 102 can be an additional implant coupled to an existing stimulator or can be a complete stimulator with incorporated control module. In certain examples, the implantable position device 502 can control electrode 504 position in or out of the sheath 540 by extruding the electrode 504 between two drive wheels or a drive wheel and an idler wheel of a drive wheel assembly. An array of actuators or mandrels of a steering assembly can control tension on pull wires or actuators within the walls of the sheath positioning the sheath through multi planar bending in both the rostral-caudal, anterior-posterior, and importantly medial-lateral spans aiming to improve stimulation pain targeting, focus the stimulation field, decrease implanted lead number/size, and decrease unwanted paresthesia or side effects. The repositioning ability of the implant positioning device 502 is advantageous to fine tuning the location of the electrode array or tip within the patient without subsequent surgery.

Figure 6A:
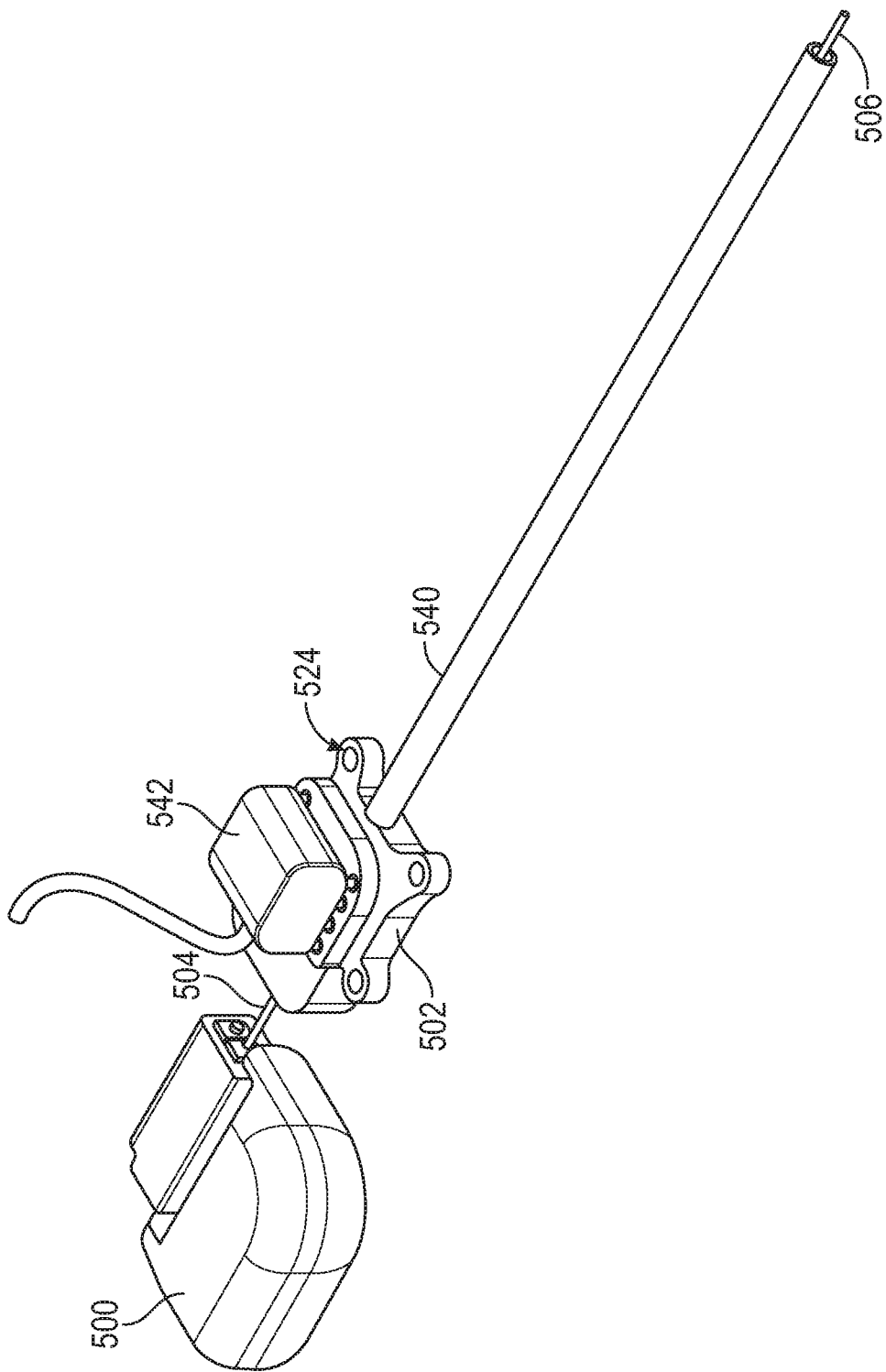
FIGS. 6A-6E are illustrations of an implant positioning device stimulator, and adjustable/positionable sheath, in accordance with an example embodiment of the present disclosure.
Figure 6B:
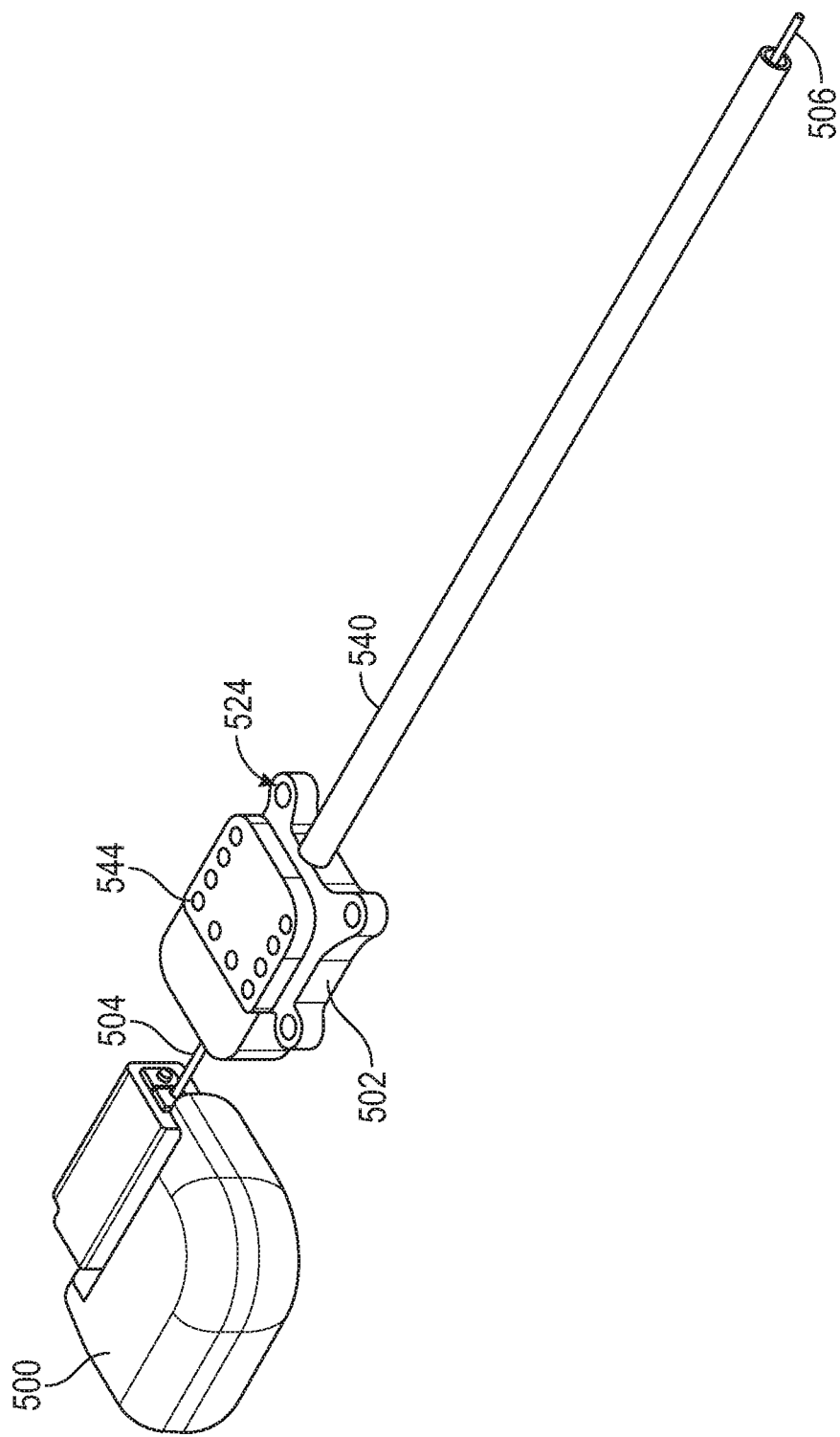
Figure 6C:
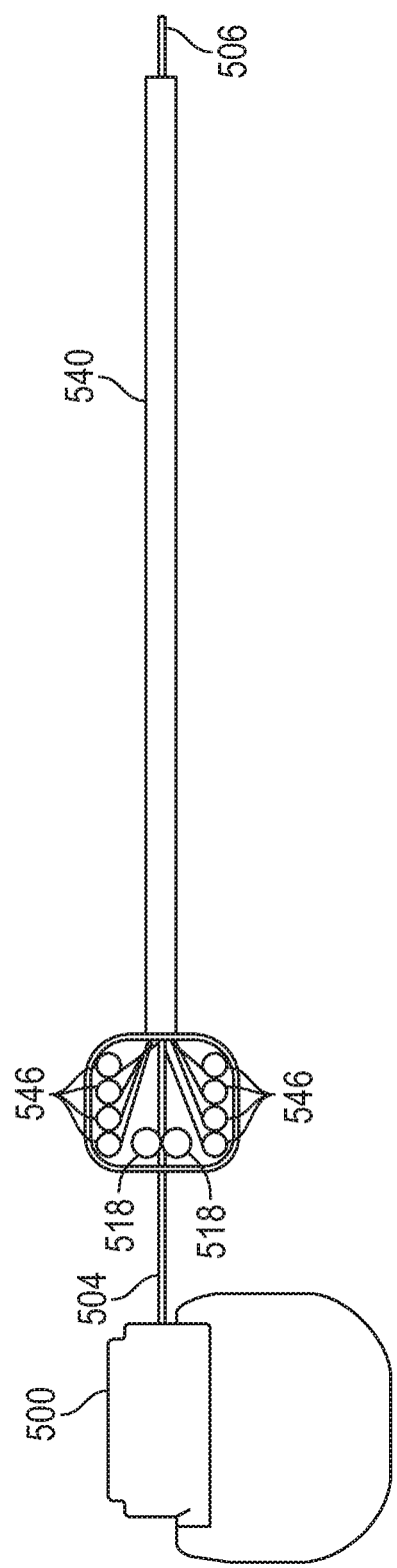
Figure 6D:
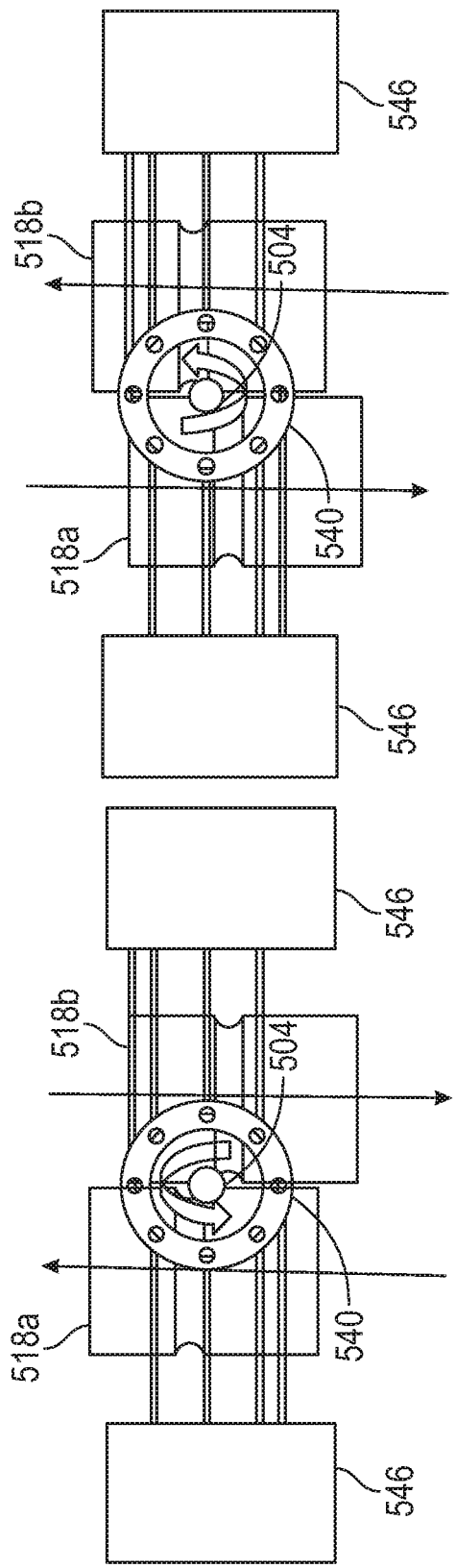
Figure 6E:
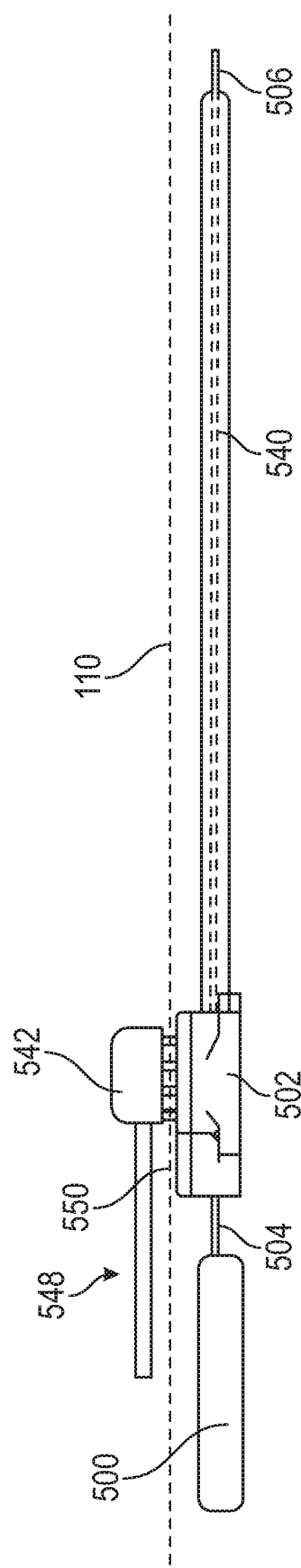

FIGS. 6A-6E are illustrations of an implant positioning device 502 stimulator 500, and adjustable/positionable sheath 540, in accordance with an example embodiment of the present disclosure. The control of the sheath 540 is enabled via an array of actuators 546 of the positioning device 502 controlling the tension of pull wires along the walls of the sheath 540. Drive wheels 518 can advance and retract the electrode 506 into and out of the adjustable sheath 540. The array of actuators 546, 518 can be manipulated by motors housed within the implanted positioning device 502 or via percutaneous engagement of motors outside the patient. FIG. 6E illustrates the implant positioning device 502 stimulator 500, and adjustable/positionable sheath 540 under the skin 110 of a patient with the electrode 506 extending with the spine of the patient. A percutaneous motor module 542 is connected to the implant positioning device 502 via trocar access channels 550. Percutaneous access to the positioning module can avoid the need to implant motors and electronics as well as minimizing degradation of internal components. The percutaneous motor module can be connected to a control system or computer via a power and communication cable 548 such as a USB cable in certain examples.

In the case of spinal cord stimulators 500, the paresthesia effect is best with optimal orientation of the stimulating electrode tips 506 facing the nerves needing stimulation. Referring to FIG. 6D, by controlling the vertical position of the drive wheels 518a, 518b the orientation of the electrode tips 506 can be controlled to face any direction such as by rotating the electrode about a longitudinal axis that is parallel to the insertion direction of the electrode. In certain examples, actuators coupled to the drive wheel 518a, 518b can offset the drive wheels to rotate the electrode.

Figure 7:
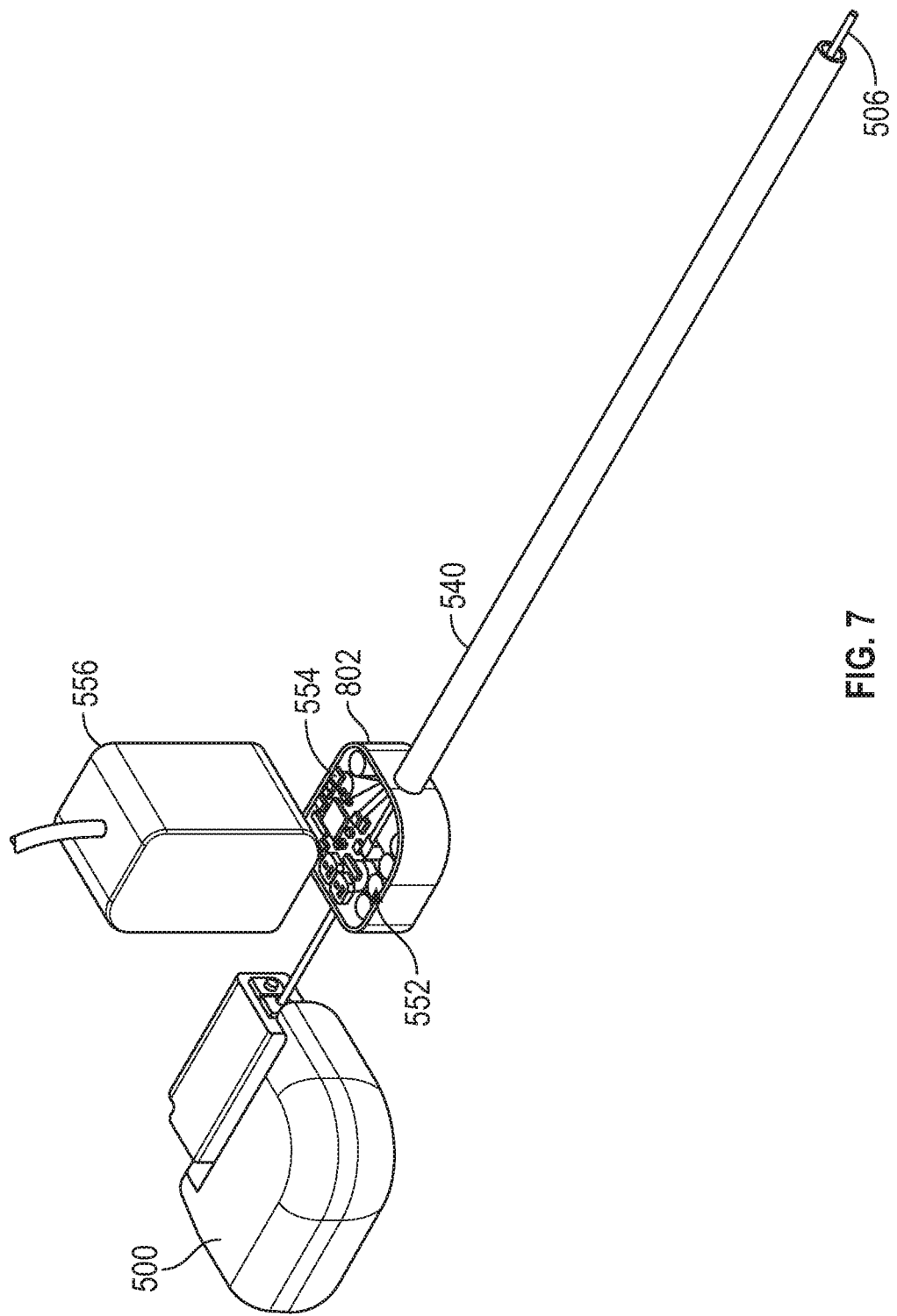
FIG. 7 illustrates an example positioning device that can include positioning circuitry and motors in addition to the actuator array.

FIG. 7 illustrates an example positioning device 702 that can include positioning circuitry and motors 554 in addition to the actuator array 552. The actuator array can include wire pull mandrels, drive wheels, drive wheel vertical actuators or combination thereof. As with the examples of FIGS. 6A-6E, an electrode and electrode tip 506 connected to a stimulation controller 500 can extend through the actuator array 552 of the positioning device and through the adjustable sheath 540. A transcutaneous power supply 556 can be used to power an implanted battery of the implant positioning device and to communicate between the processing unit of the positioning device 802 and an external surgeon user interface. It is understood that the implant positioning device 802 is shown without a cover for illustrative purposes.

FIG. 8A-8D illustrates generally various states of a modular sheath and electrode positioning device in accordance with the present subject matter. The illustrated system can include a sheath drive module 858 and an electrode positioning module 862. The sheath drive module 858 can include screw/suture points 824, and sheath drive wheels 860. The electrode positioning module 862 can include screw/suture points 824, one or more steering mandrels 846, one or more electrode drive wheels 818, and an optional electrode chamber 864. The system depicted in FIG. 8A would typically have the sheath drive module 858 secured to a surgical site on the patient. The sheath drive wheels 860 can advance the sheath 840 and connected electrode positioning module 862, into the patient (FIG. 8B). During advancement of the sheath 840, steering mandrels 846 within electrode positioning module 862 can control orientation and position of the tip of the sheath 840, or entire length of the sheath 840, depending on fulcrum points which may vary along the length of the sheath 840 (FIG. 8C). Once the sheath 840 has been advanced to the target site, electrode positioning module 862 can be secured to the patient and the electrode drive wheels can be controlled to advance the electrode 804 out of or back into the adjustable sheath 840 (FIG. 8D). In certain examples, the sheath 840 may have motion capture fiduciary markers 866 (radiographic attenuating, optically reflective, metallic, or optical cameras at the tip or along the length to observe and characterize insertion states, thereby enabling support for closed loop robotic position control of the sheath shape. In certain examples, the sheath 840 may fully enclose the electrode 804. In some examples, the sheath 840 may allow the electrode 804 to protrude and extend past the end of the sheath 840.

Figure 9A:
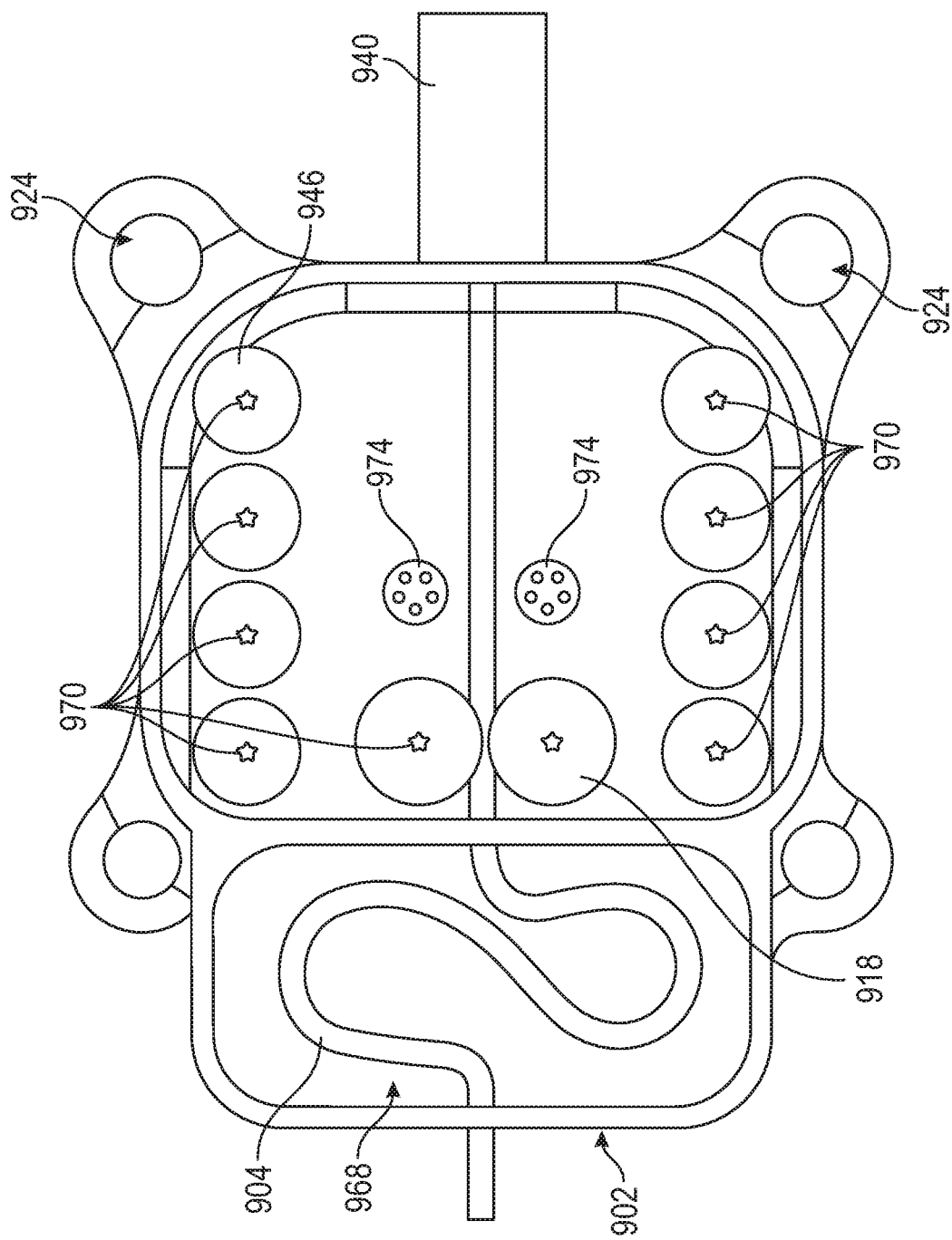
FIGS. 9A-9C illustrate generally various examples of a modular electrode positioning device according to the present subject matter.
Figure 9B:
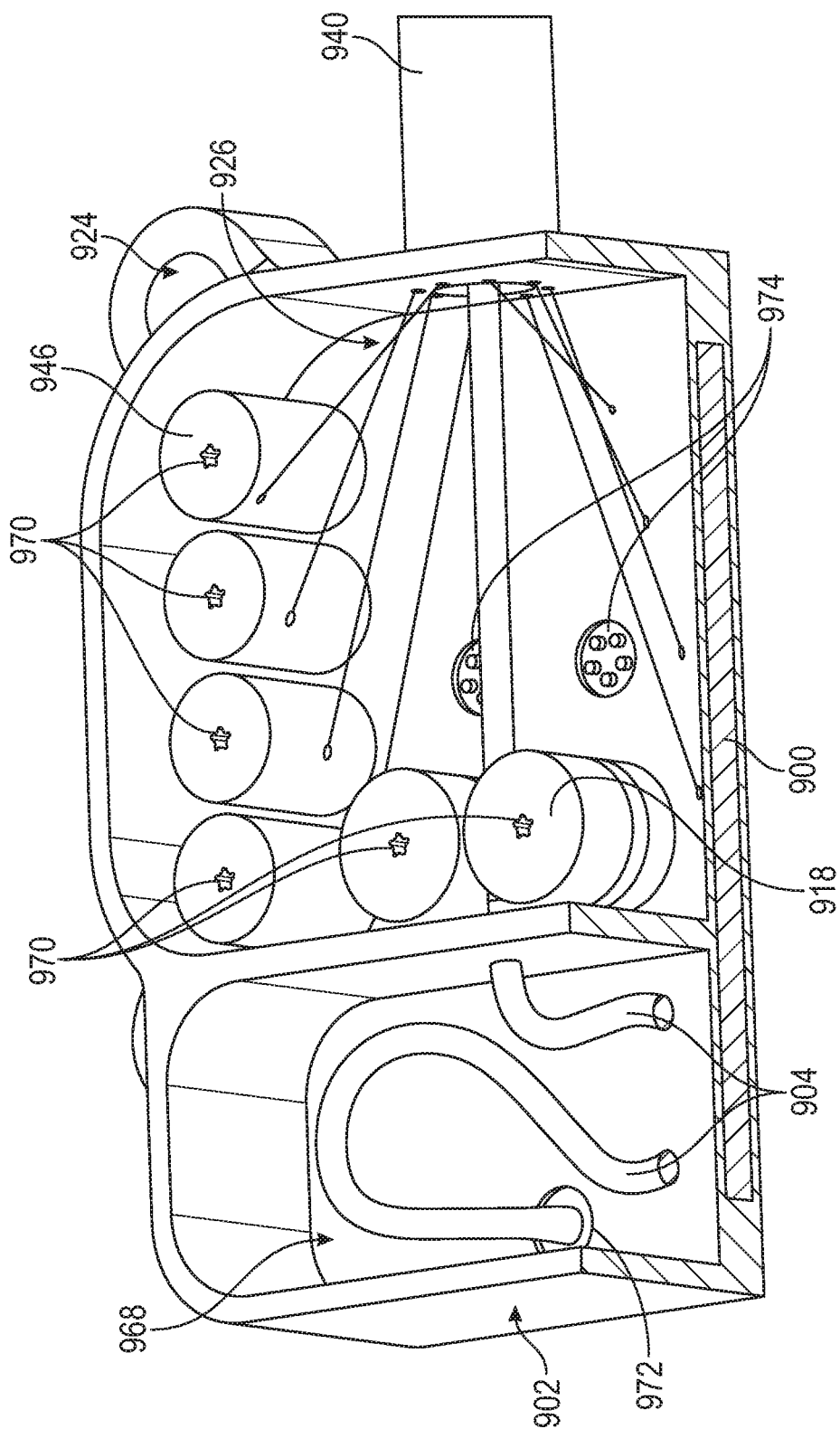

FIGS. 9A and 9B illustrate generally various examples of a modular electrode positioning device according to the present subject matter. FIG. 9A illustrates a modular electrode positioning device 902, without a cover, that can be employed with a second, separate module that houses the stimulation electronics. FIG. 9B illustrates a cut-away view of a modular electrode positioning device 902, without a cover, that includes integrated neuromodulator circuitry 900. Each example of the electrode positioning device 902 can include screw/suture points 924, multiple steering mandrels 946 coupled to pull wires 926 of an adjustable sheath 940, one or more electrode drive wheels 918. and an electrode chamber 968. Mechanical engagement points 970 can assist in positioning of the electrode 904 or the sheath 940. By introducing a mechanical bit connected to a motor that mates with the mechanical engagement points 970 of the mandrels 946 and/or drive wheels 918 through a trocar and self-sealing septum, the position of the sheath 940 or the tip of the electrode 904 can be manipulated and precisely located. An electrical engagement point 974 within the device can allow for powering of batteries and communication with implanted motors (not shown) to control position of the sheath 940 or the tip of the electrode 904. The electrical engagement points 974 can be accessed through a trocar and self-sealing septum. An electrode chamber 968 may be occupied by an excess length of electrode 904 that can be used to reposition the electrode tip deeper within the patient.

A wall of the electrode chamber can include a hermetic electrical feedthrough from the integrated neuromodulator circuit 900.

Figure 9C:
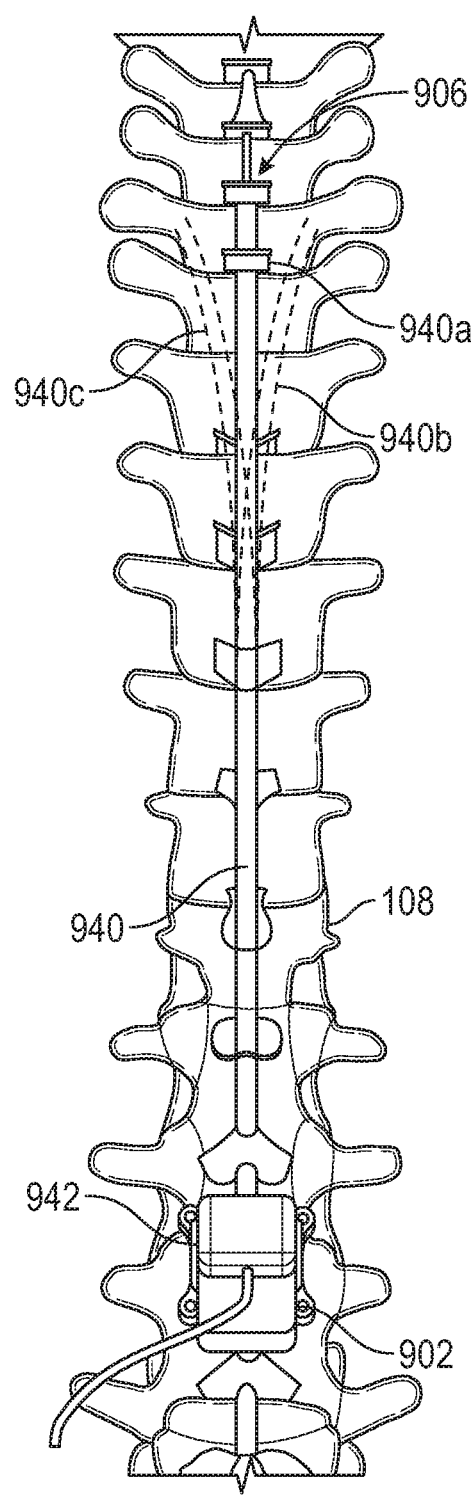

FIG. 9C illustrates generally a state of an example of a modular electrode positioning device during an insertion or repositioning procedure. The modular electrode positioning device can include an electrode (not visible) with an electrode tip 906, a sheath 940, an implant electrode positioning device 902, and a percutaneous motor module 942. The electrode tip 906 can be guided to a desired stimulation location via the sheath 940. The sheath 940 can include pull wires coupled to steering mandrels of the implant electrode positioning device 902. As the sheath 940 is inserted, the percutaneous motor module 942 can be coupled to the implant electrode positioning device 902 and motors of the implant electrode positioning device 902 can actuate the steering mandrels to steer the lateral direction of the implanted sheath 940. Lateral steering capability is illustrated by a few of the many directions 940a, 940b, 940c the sheath could be directed via operation of the pull wires of the implant electrode positioning device 902. Upon the electrode tip 906 reaching a desired location along the spine 108, the percutaneous motor module 942 can be removed from the implant electrode positioning device 902, the surgical site of the implant electrode positioning device 902 can be closed, and the implant electrode positioning device 902 can begin delivering stimulation via the electrode tip 906. If adjustments to electrode position are desired or needed to optimize implant position after procedure completion, the percutaneous motor module 942 can be utilized to re-access and engage the implant electrode positioning device 902 and implanted sheath 940 to modify the sheath or electrode positions or location within the body to a target site.

FIGS. 10A-10D illustrate generally creation and use of a mechanical percutaneous implant connection port, in accordance with an example embodiment of the present disclosure. A mechanical percutaneous implant connection port can be created to access a mechanical interface to drive a drive wheel 1018, a pull wire mandrel or a steering mandrel. FIG. 10A-10D illustrate generally creation of a mechanical percutaneous implant connection port for a drive wheel, such as drive wheel of any of the example implants described herein. Creation as use of a mechanical percutaneous implant connection port for a pull wire mandrel or steering mandrel is the same as for the drive wheel except for the function of the mandrel. The drive wheel 1018 can be housed within casing of the implant 1002 and can have a companion idler wheel 1019 in certain examples. From the description above, the drive wheel 1018 can be used to extend or retract an electrode (e.g., FIG. 2, 218) or sheath (e.g., FIG. 8, 860) for an electrode into or out of the body of a patient.

Figure 10B:
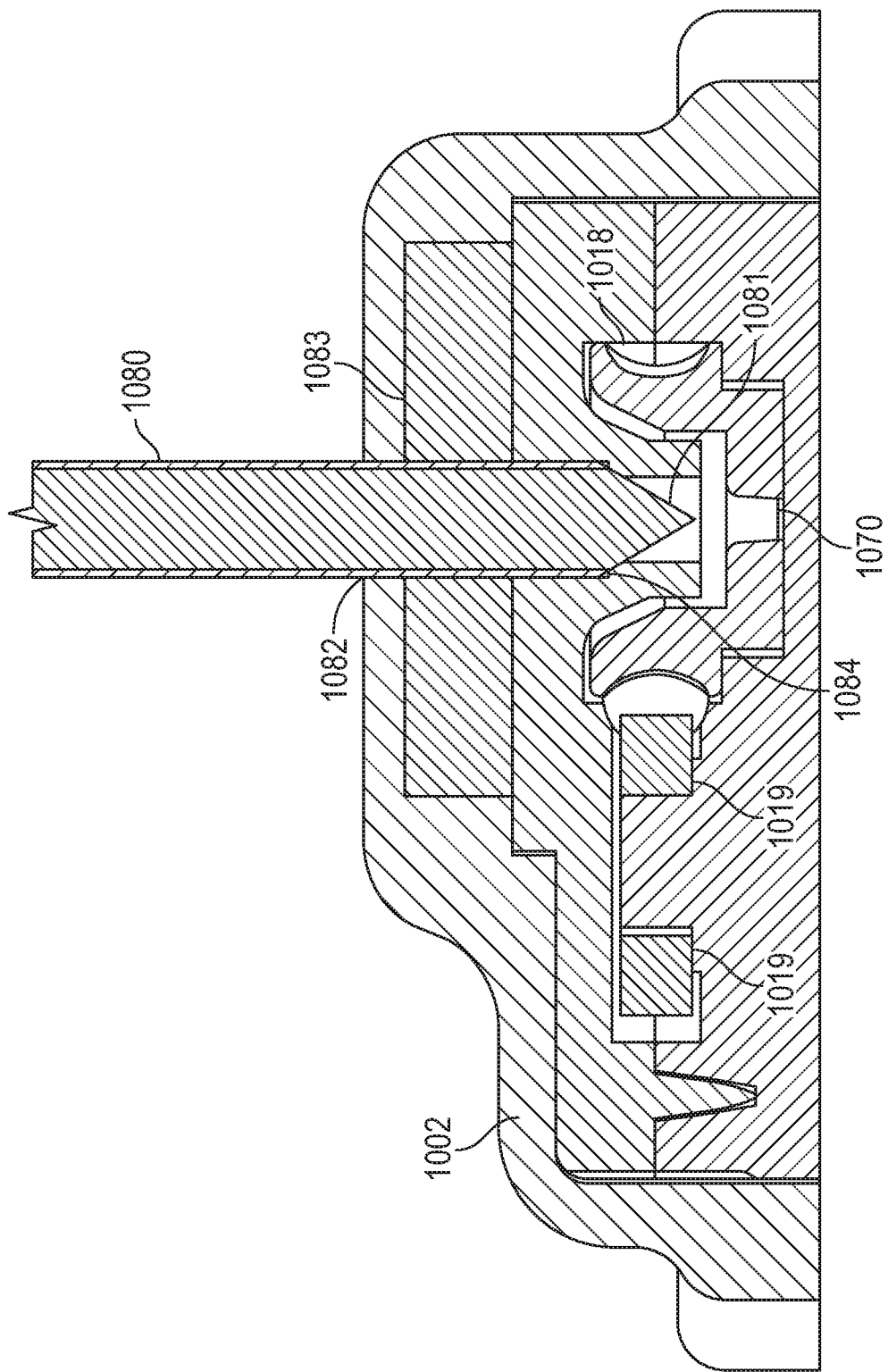
Figure 10C:
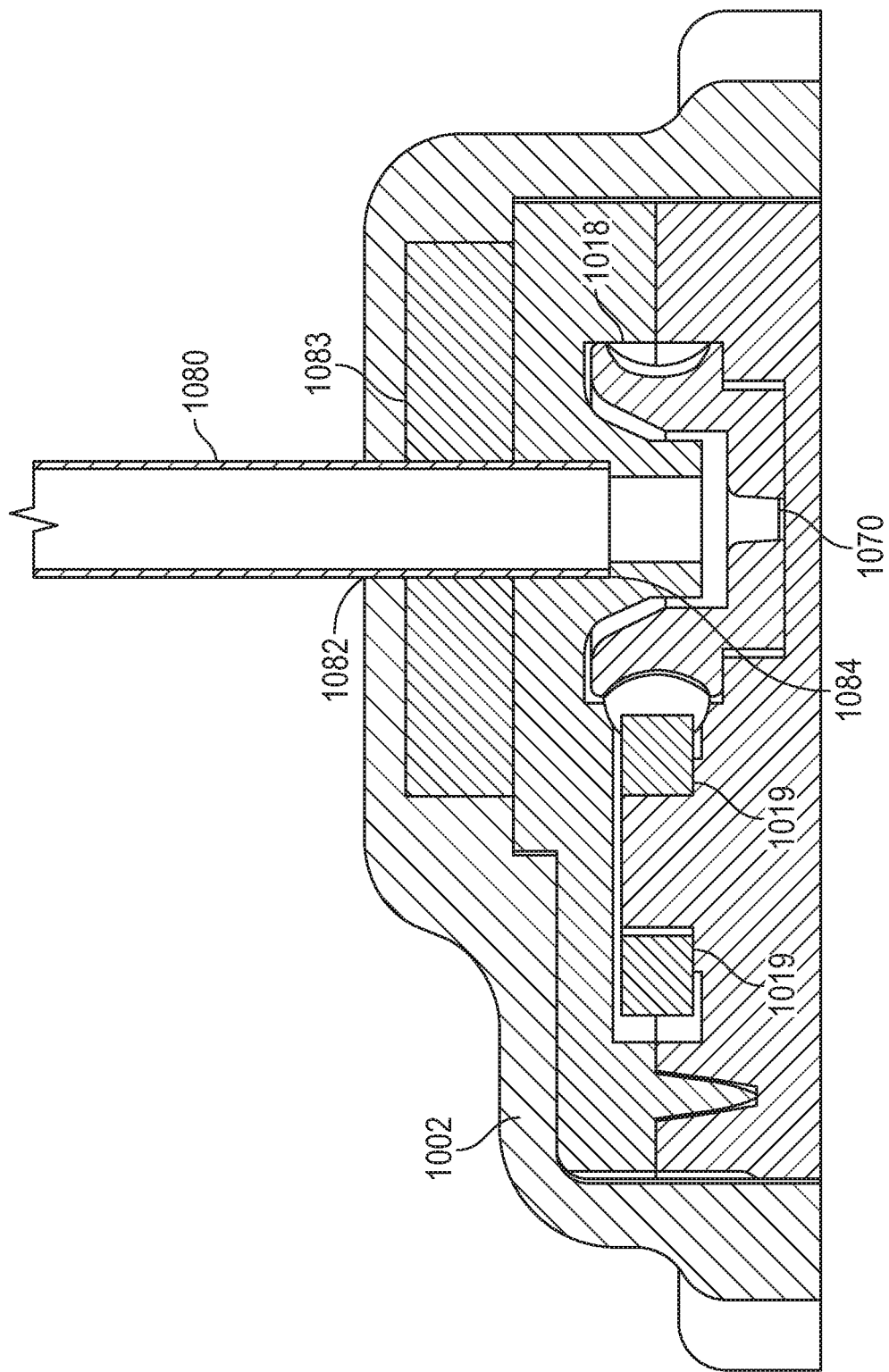

FIG. 10A illustrate generally a step in creating the mechanical percutaneous implant connection port and shows a needle 1081 piecing skin 110 above a trocar entrance 1082 of the casing of the implant 1002. The needle leads the way for a trocar 1080 to be received at the trocar entrance 1082. As illustrated in FIG. 11B, the needle and trocar can proceed past the trocar entrance 1082 and enter a self-sealing septum 1083 of the implant 1002. The trocar 1080, with the needle 1081 leading, can be proceed to a trocar stop 1084 of the implant 1002. Once the trocar 1080 is seated at the trocar stop 1084, the needle 1081 can be extracted from the trocar 1080 as illustrated in FIG. 10C to leave the trocar 1080 as a working channel into the implant 1002.

Figure 10D:
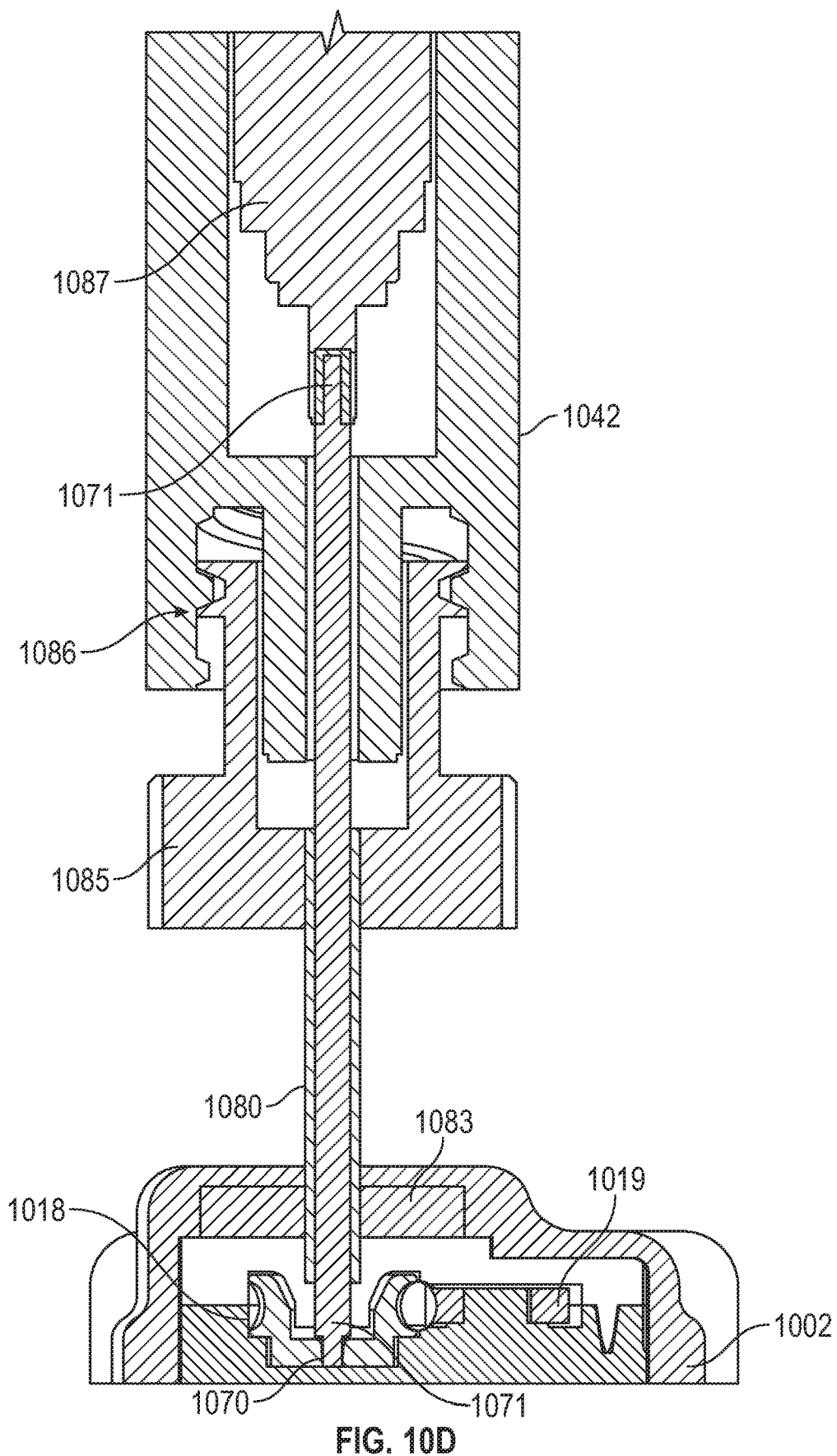

FIG. 10D illustrates use of the working channel provided by the trocar 1080. For example, a mechanical driver 1071 of a drive module 1042 can be inserted through the trocar 1080 to engage a mechanical interface 1070 of the drive wheel 1018. Upon engagement of the driver 1071 with the mechanical interface 1070 of the drive wheel 1018, a motor 1087 of the motor module 1042 can be used to move the drive wheel 1018. In certain examples, the driver 1071 can include a pentalobe tip for mechanical engagement with the drive wheel 1018 through the working channel of the trocar 1080. The pentalobe bit can be robotically rotated, linearly positioning an electrode or other elongate member of the system including the implant 1002. An external motor 1087 is pictured controlling the drive wheel 1018 through the trocar working channel in FIG. 10D. Also depicted in FIG. 10D is the leer lock quick swap mechanism 1085, 1086 for simple swapping from the needle 1081 to the mechanical driver 1071. Once the electrode, or sheath, is in position, the mechanical driver 1071 and trocar 1080 can be removed allowing the septum 1083 to seal again. By providing a sealed compartment to house the various drive wheels, pull wire mandrels, steering mandrels, electronics engagement points, or combinations thereof, tissue ingrowth and foreign body encapsulation are thereby prevented around the moving or electrical parts.

FIGS. 11A-11D illustrate generally creation and use of an electrical percutaneous implant connection port, in accordance with an example embodiment of the present disclosure. An electrical percutaneous implant connection port can be created to access a electrical connector or feedthrough 1188 of an implant for distribution of power and communications between the circuitry 1100 of the implant 1102 and controls or interfaces external to the patient. FIG. 10A-10D illustrate generally creation of an electrical percutaneous implant connection port for connection with a electrical connector or feedthrough 1088 of any of the example implants described herein.

Figure 11A:
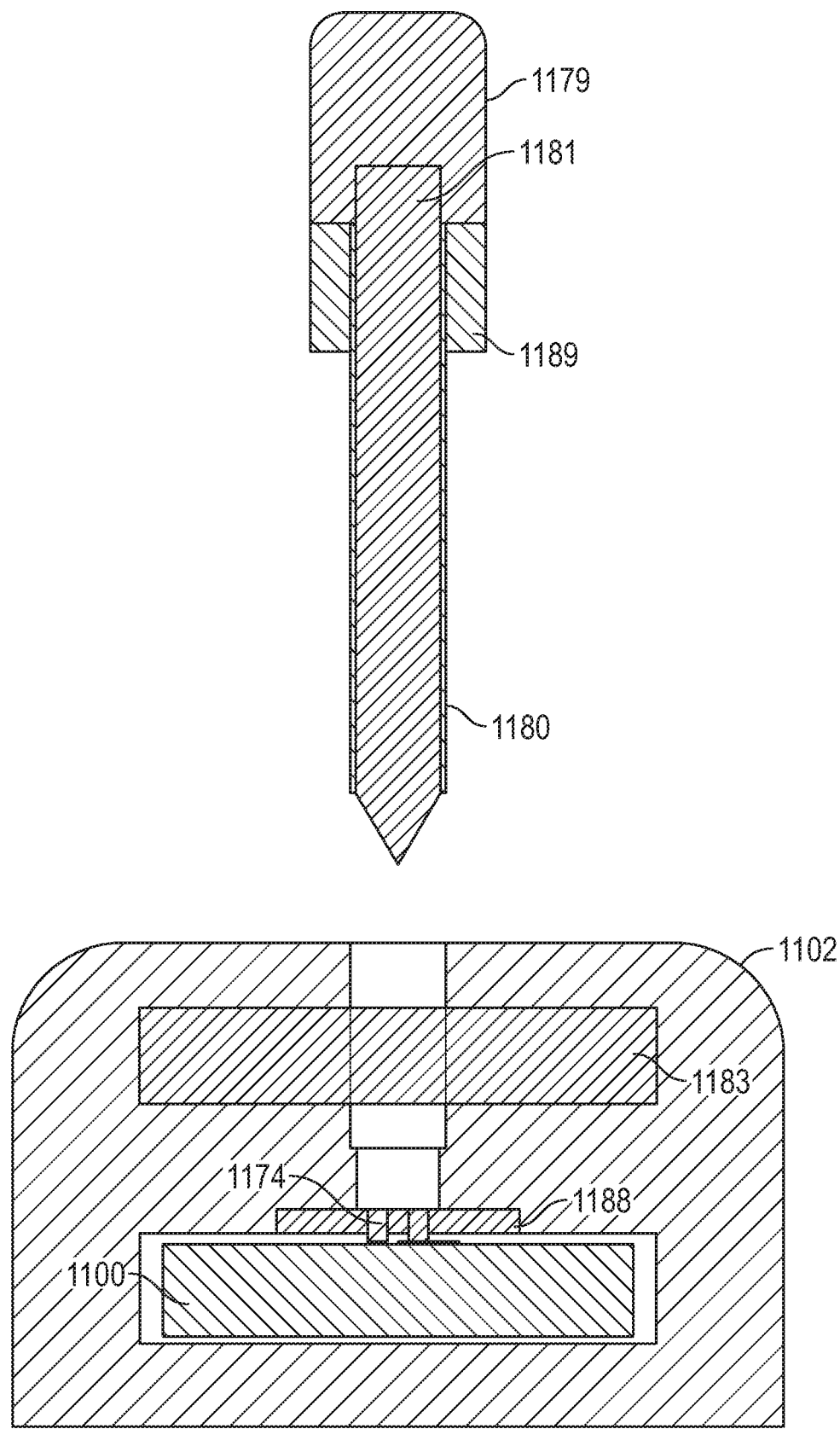
FIGS. 11A-11D illustrate generally creation and use of an electrical percutaneous implant connection port, in accordance with an example embodiment of the present disclosure.
Figure 11B:
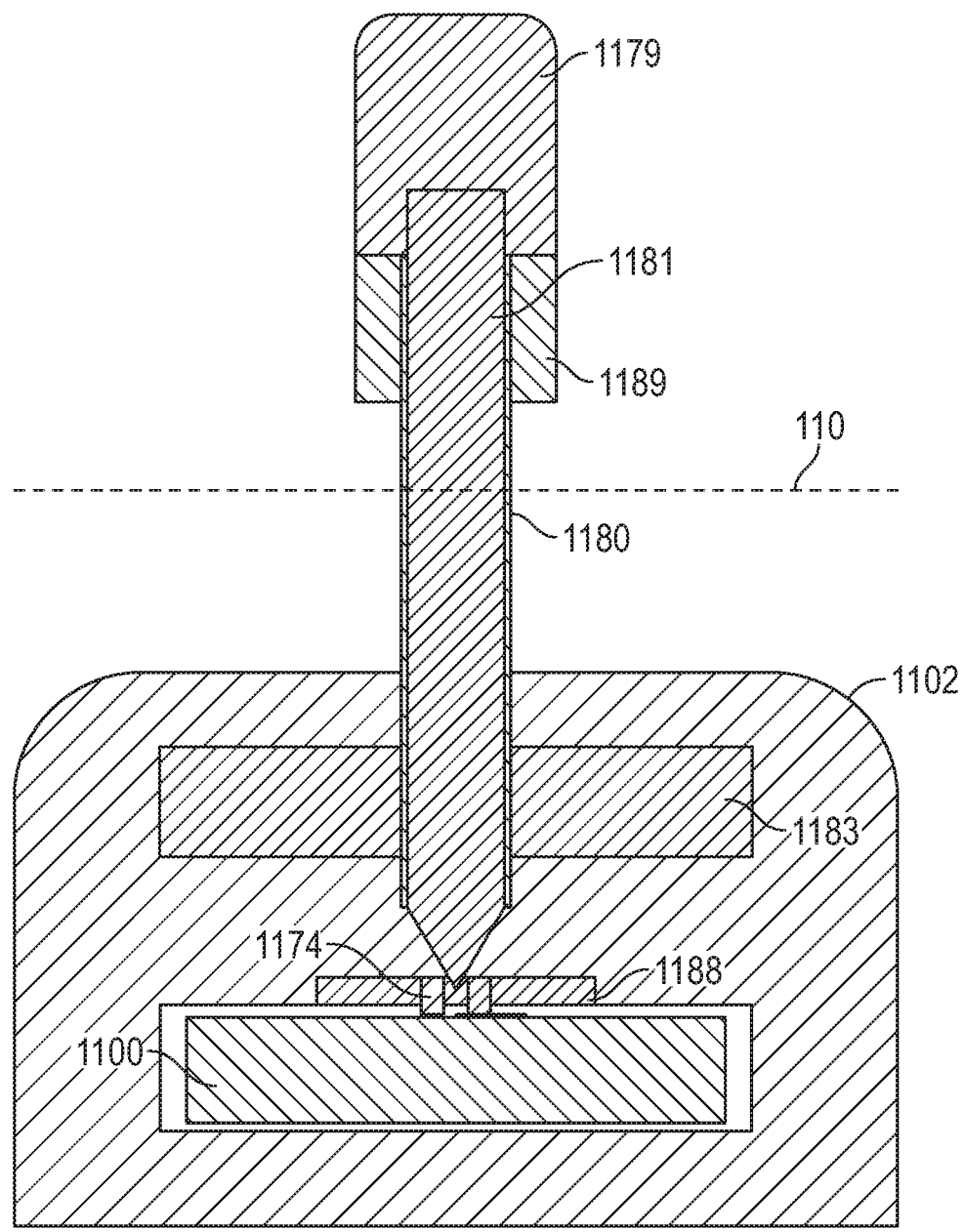
Figure 11C:
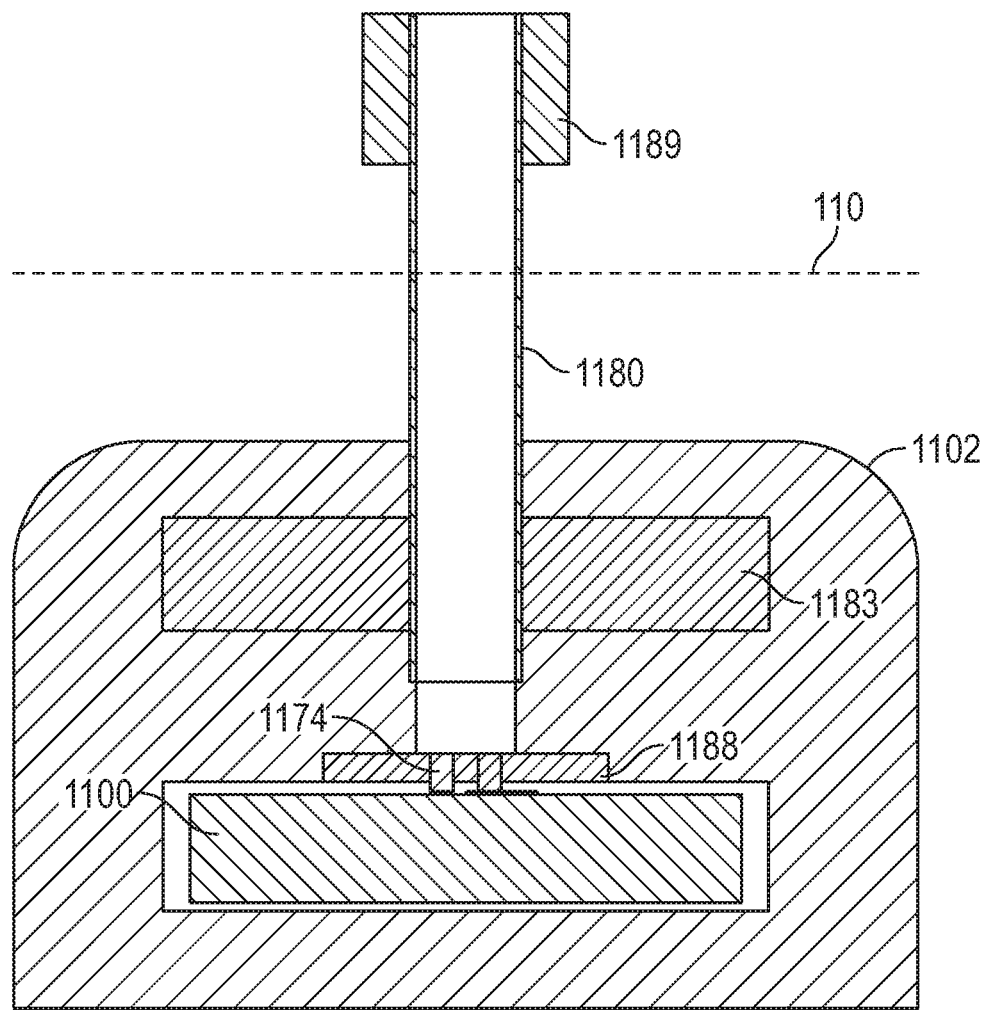
Figure 11D:
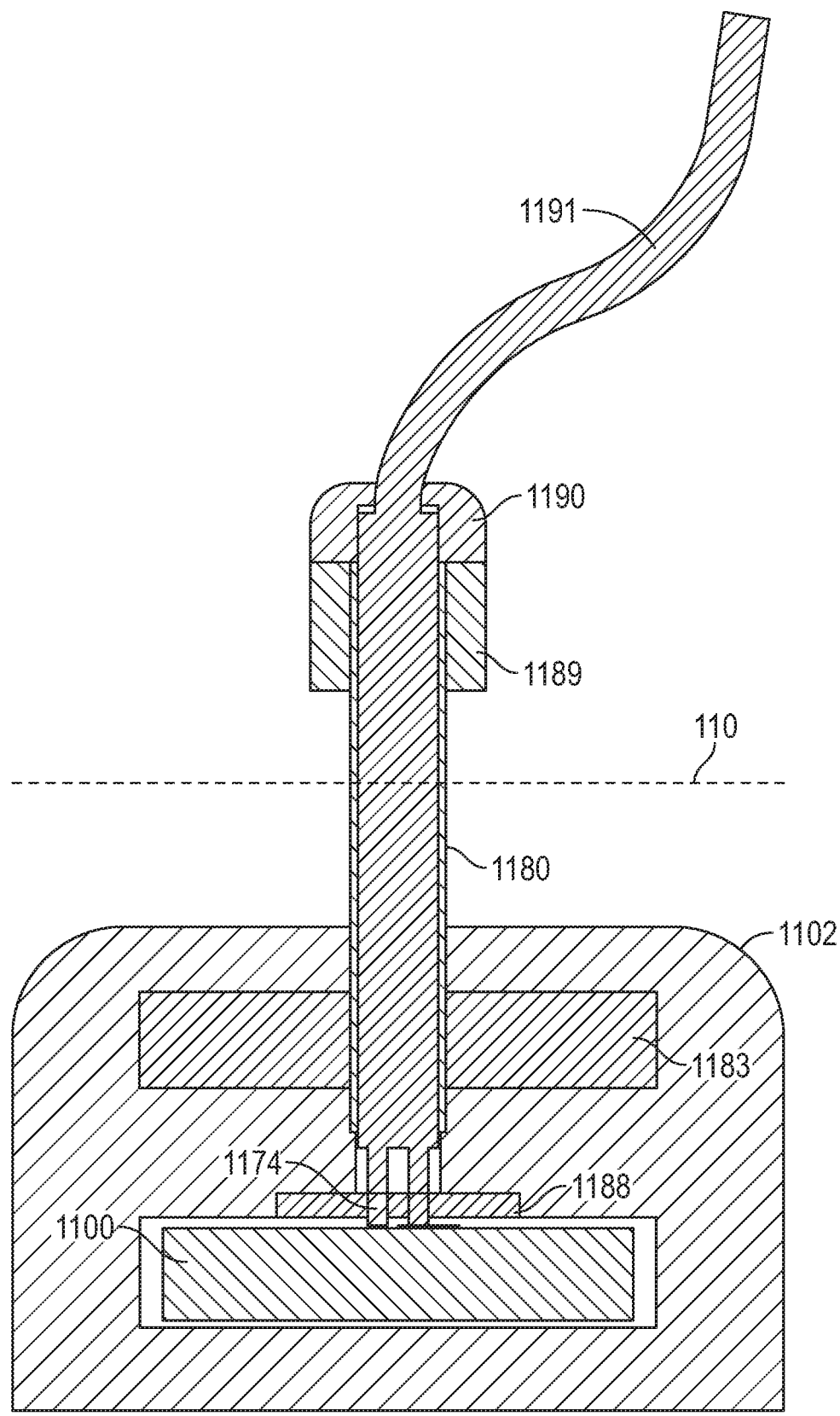

FIG. 11A illustrate generally a step in creating the electrical percutaneous implant connection port and shows a needle 1181 piecing skin 110 above a trocar entrance of the casing of the implant 1102. The needle 1181 can lead the way for a trocar 1180 to be received at the trocar entrance. As illustrated in FIG. 11B, the needle 1181 and trocar 1080 can proceed past the trocar entrance and enter a self-sealing septum 1183 of the implant 1102. The trocar 1180, with the needle 1181 leading, can be proceed to a trocar stop 1184 of the implant 1102. Once the trocar 1180 is seated at the trocar stop 1184, the needle 1181 can be extracted from the trocar 1180 as illustrated in FIG. 11C, to leave the trocar 1080 as a working channel into the implant 1002. In certain examples, the trocar can include a cover 1179 to prevent foreign materials from entering the trocar 1080 during creation of the working channel. In certain examples, the trocar 1080 can include a coupling 1189 for engagement with a interface connector of the power or communication cable 1191 of the device to be electrically coupled with the electrical connector or feedthrough 1074 of the implant 1102 as shown in FIG. 11D.

Figure 12A:
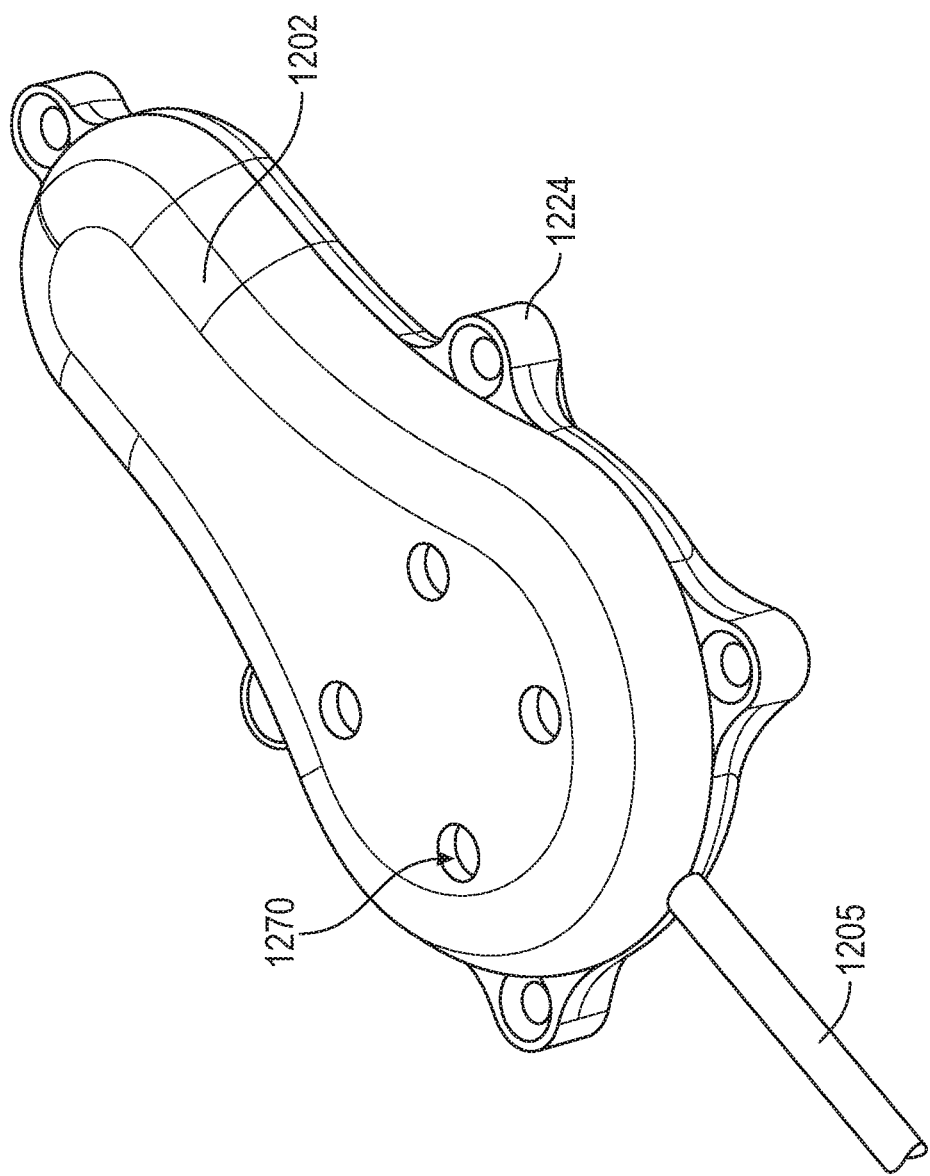
FIG. 12A illustrates generally an implant positioning device, the implant, and adjustable lead of a deep brain stimulator system (DBS).
Figure 12B:
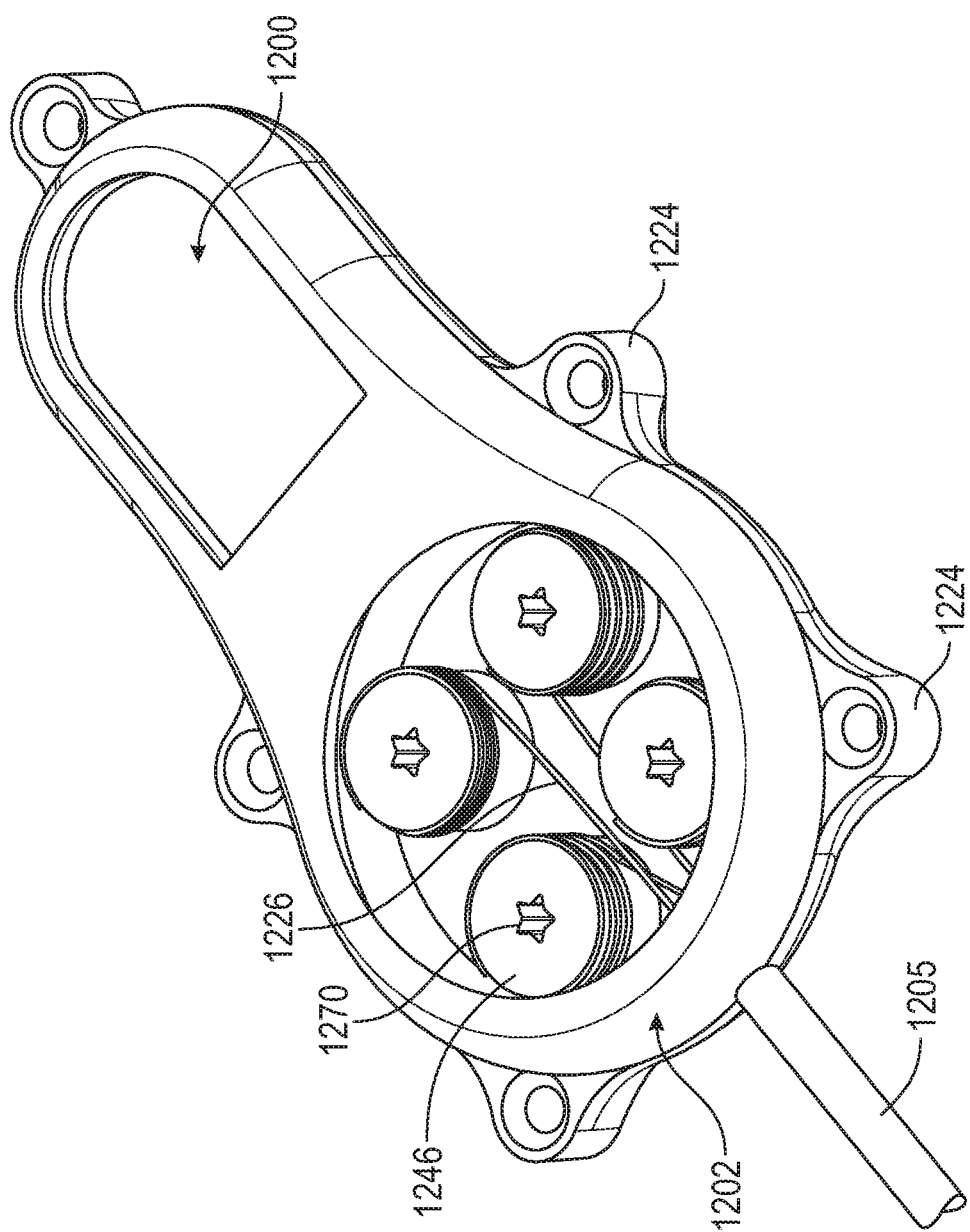
FIG. 12B illustrates generally the implant with a cover removed.

FIG. 12A illustrates generally an implant positioning device, the implant 1202, and adjustable lead 1205 of a deep brain stimulator system (DBS). FIG. 12B illustrates generally the implant 1202 with a cover removed. The exterior of the implant can include screw/suture points 1224 and mechanical connection ports 1282 for receiving a driver 1271 for driving steering mandrels 1246 of the implant 1202. The steering mandrel can extend or retract pull wires 1226 connected to the adjustable lead 1205. In certain examples, the implant 1202 can include stimulator circuitry 1200 for electrically stimulating the adjustable lead 1205.

Figure 12C:
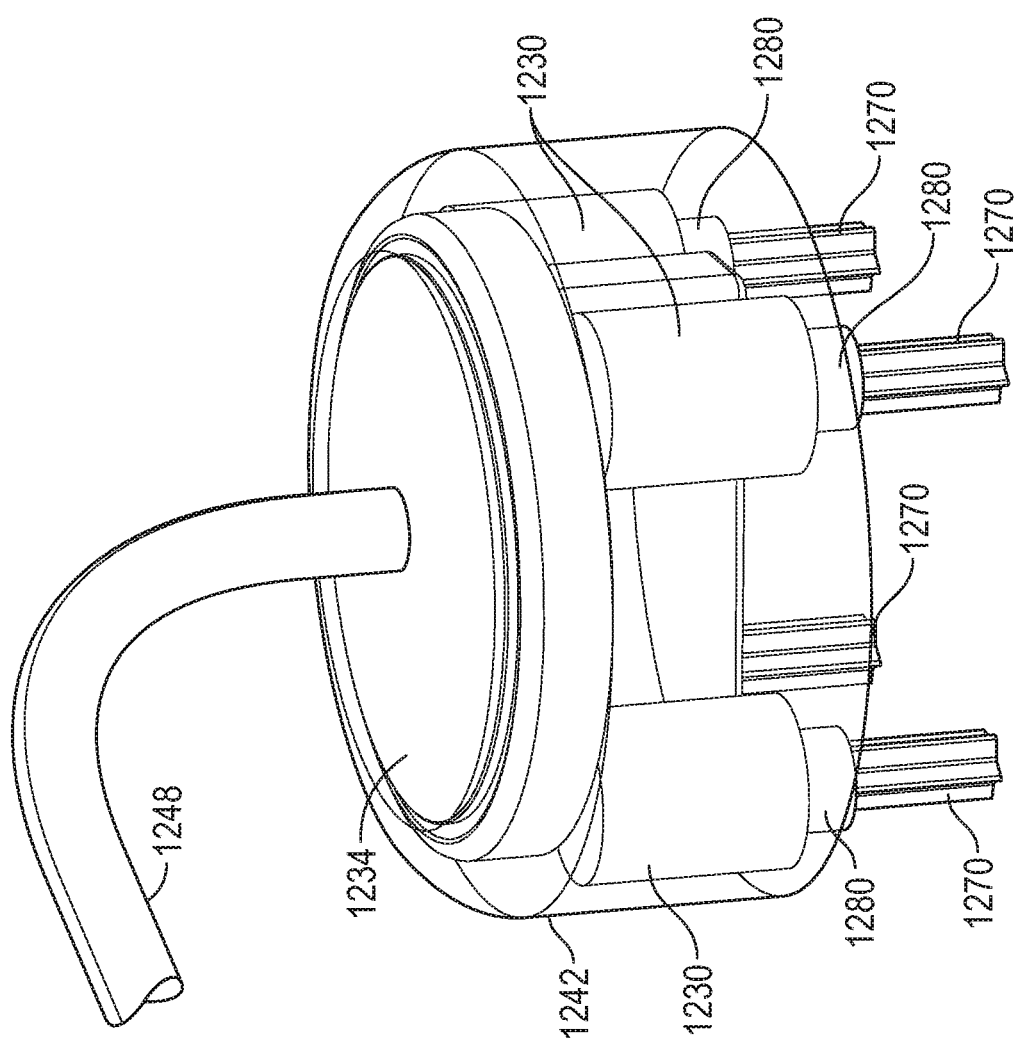
FIG. 12C illustrates generally a motor control module for temporary or percutaneous attachment to the implant.

FIG. 12C illustrates generally a motor control module 1242 for temporary attachment to the implant 1202. The motor control module 1242 is attached to the implant 1202 when initially positioning the tip of the adjustable lead 1205 within the brain of a patient and when repositioning the tip of the adjustable lead 1205. The motor control module 1242 can include motors 1230 and drive bits 1271 for mechanically moving the steering mandrels of the implant. A access canula 1280 can assist coupling a corresponding drive bit 1271 with the respective connection port 1282 of the implant 1202. A cable 1248 can provide power and communication to the motors 1230 and related circuitry of the motor control module 1242. In certain examples, the related circuitry (not shown) can include processing circuitry and position sensors to assist in controlling the direction of the adjustable lead 1205 as the lead is inserted into the brain of the patient. In certain examples, the cable 1248 cab be a universal serial bus (USB) cable.

Figure 13A:
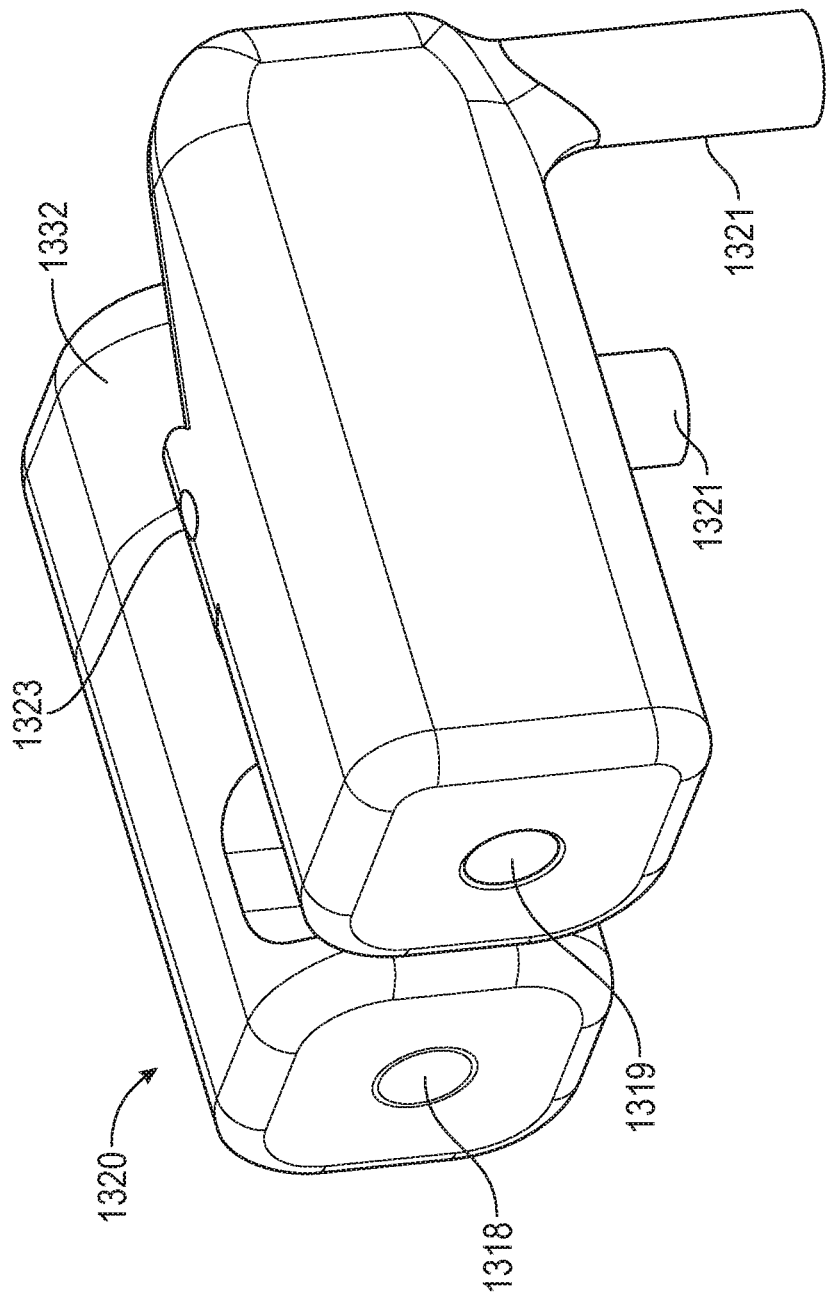
FIGS. 13A and 13B illustrate generally an example insertion device of an example of a DBS system.
Figure 13B:
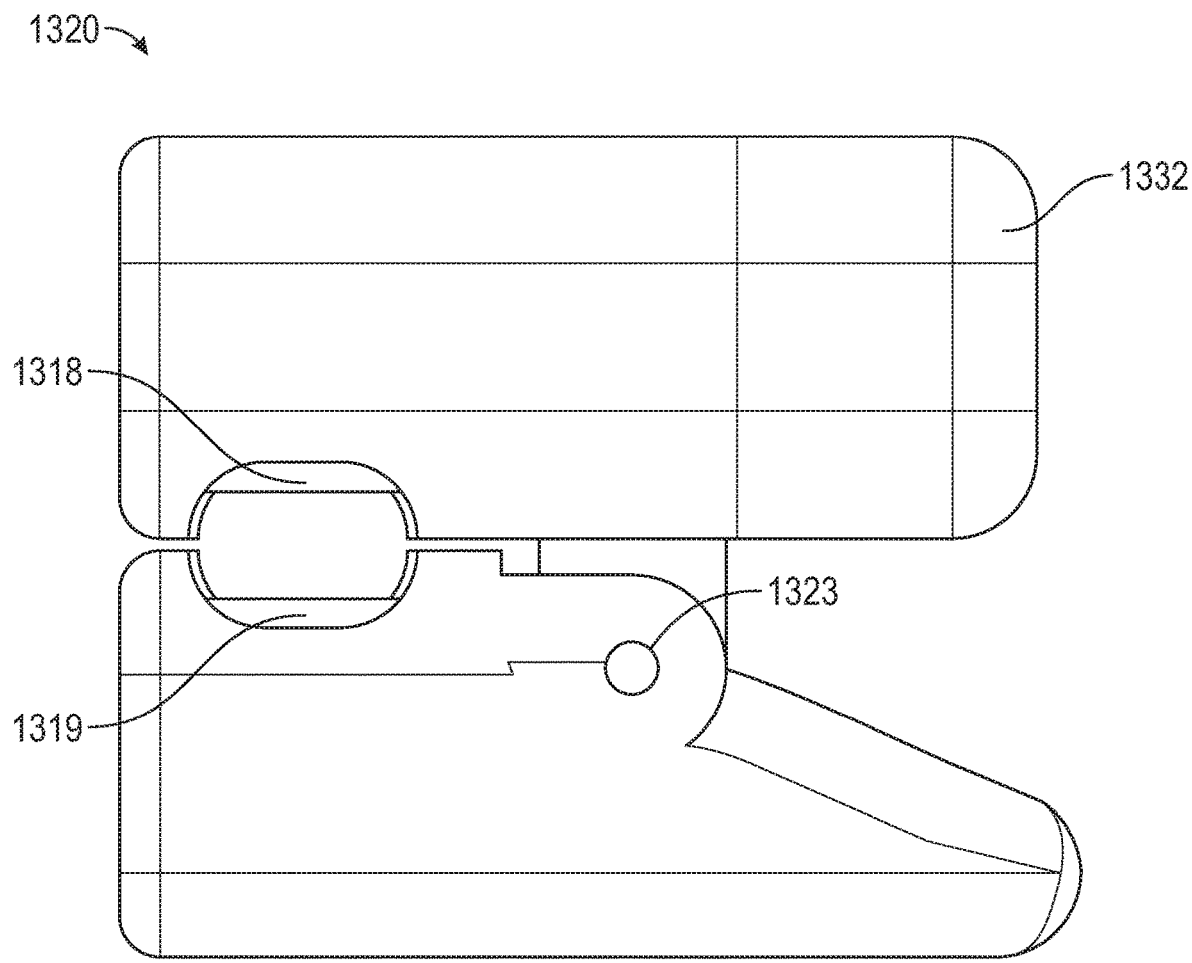

FIGS. 13A and 13B illustrate generally an example insertion device 1320 of an example of a DBS system. The insertion device 1320 can include a motor 1332, a drive wheel 1318, an idler wheel 1319, a clip hinge 1323 and one or mor burr hole fixation points 3121. The insertion device 1320 can be clipped on to the adjustable lead (FIG. 12, 1205) and secured to a burr hole plate (FIG. 14A, 1490) or the head of the patient, via the burr hole fixation points 1321, to provide the insertion motion for positioning the adjustable lead. In certain examples, the spring-loaded clip hinge 1323 can allow the drive wheel 1318 and idler wheel 1319 to be separated from each other for clipping of unclipping the insertion device on the adjustable lead. When the insertion device 1320 is clipped to the adjustable lead 1205, the spring-loaded clip hinge 1323 can clamp adjustable lead between the drive wheel 1218 and the idler wheel 1219. The motor 1332 can provide the mechanical force to insert and retract the adjustable lead. In some examples, the insertion device 1320 can include position sensors, such as encoders to provide precise velocity and position control of the motor 1332. A cable (not shown) of the insertion device 1320 can provide power and communications.

Figure 14A:
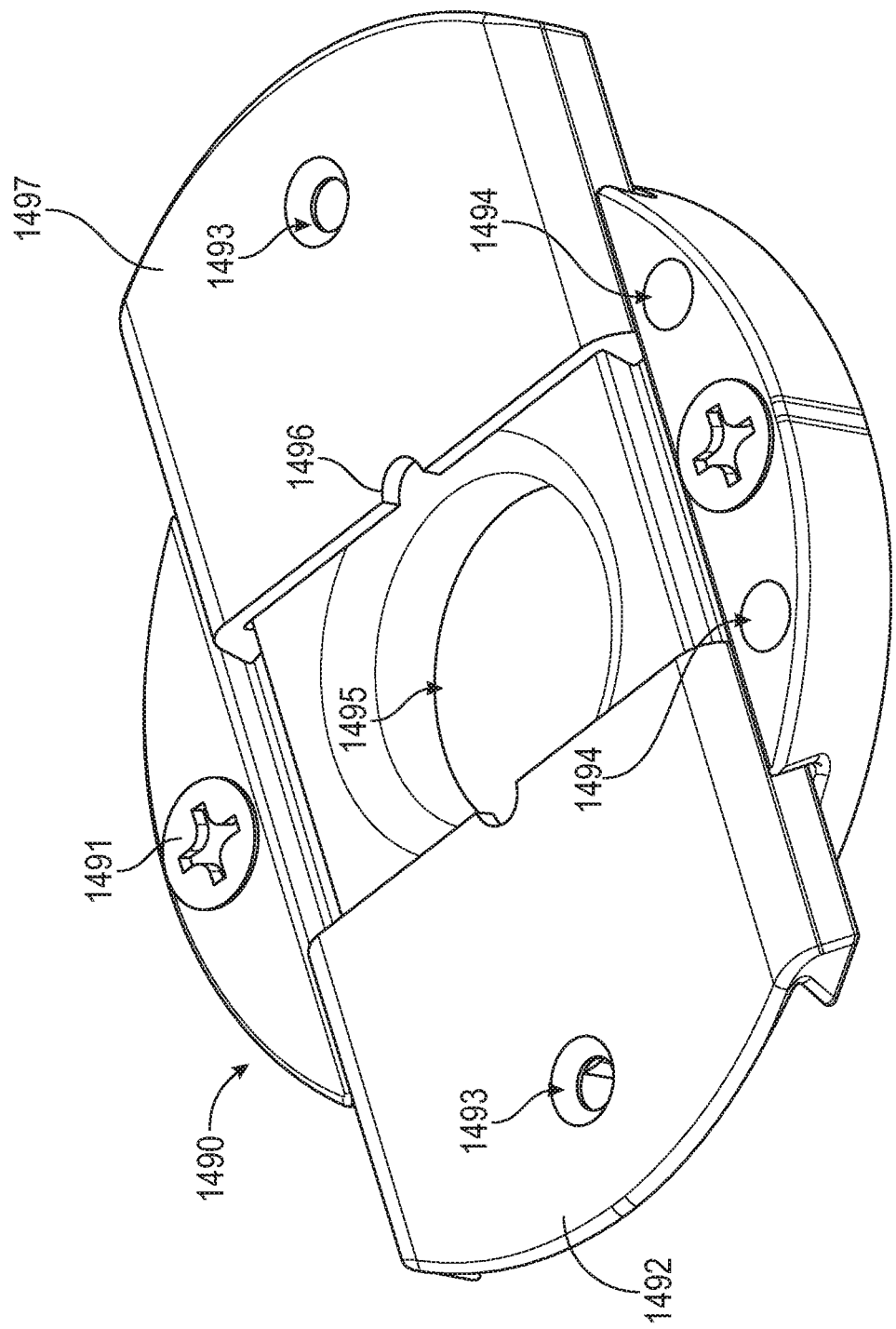
FIGS. 14A and 14B illustrate generally an example burr hole plate for anchoring certain components of an example DBS system to a patient.
Figure 14B:
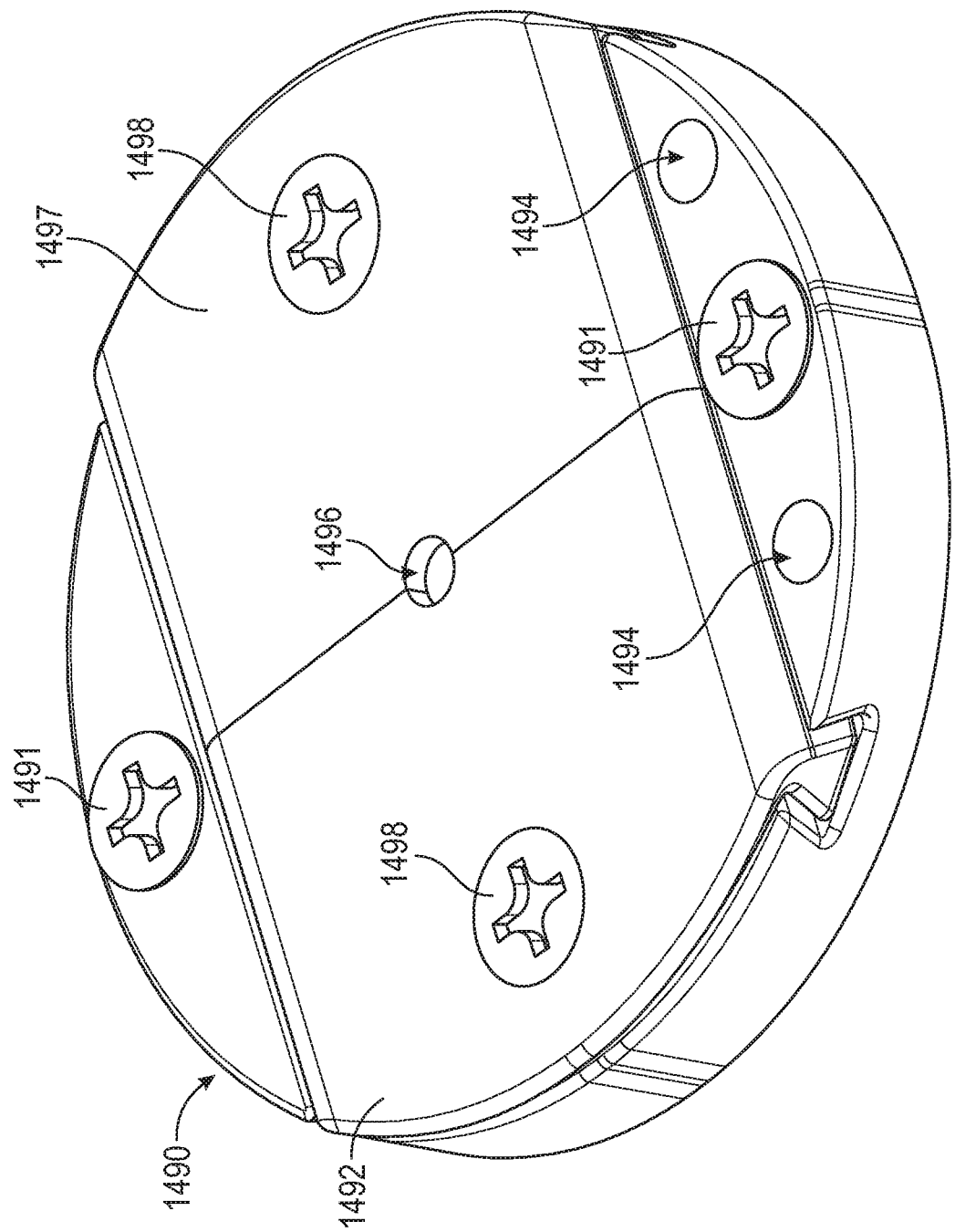

FIGS. 14A and 14B illustrate generally an example burr hole plate 1490 for anchoring certain components of an example DBS system to a patient. The burr hole plate can include fixation points 1494 for the insertion device (FIG. 13A, 1320), bone screws 1491, and sliding plates 1492, 1497. The bone screws 1491 can couple the burr hole plate to the patient. The slides 1492, 1497 can allow access to a burr hole in the head of a patient in an open position and can cover the burr hole in a closed position. The slides 1492, 1497 can include secure holes 1493 and notches 1496. The secure holes 1493 can allow the slides 1492, 1497 to be secured in the closed position with additional screws 1498. In the closed position, the notches 1496 can secure and fix the adjustable lead (FIG. 12A, 1205) between the slides 1492, 1497 after the tip of the adjustable lead has been positioned.

Figure 15A:
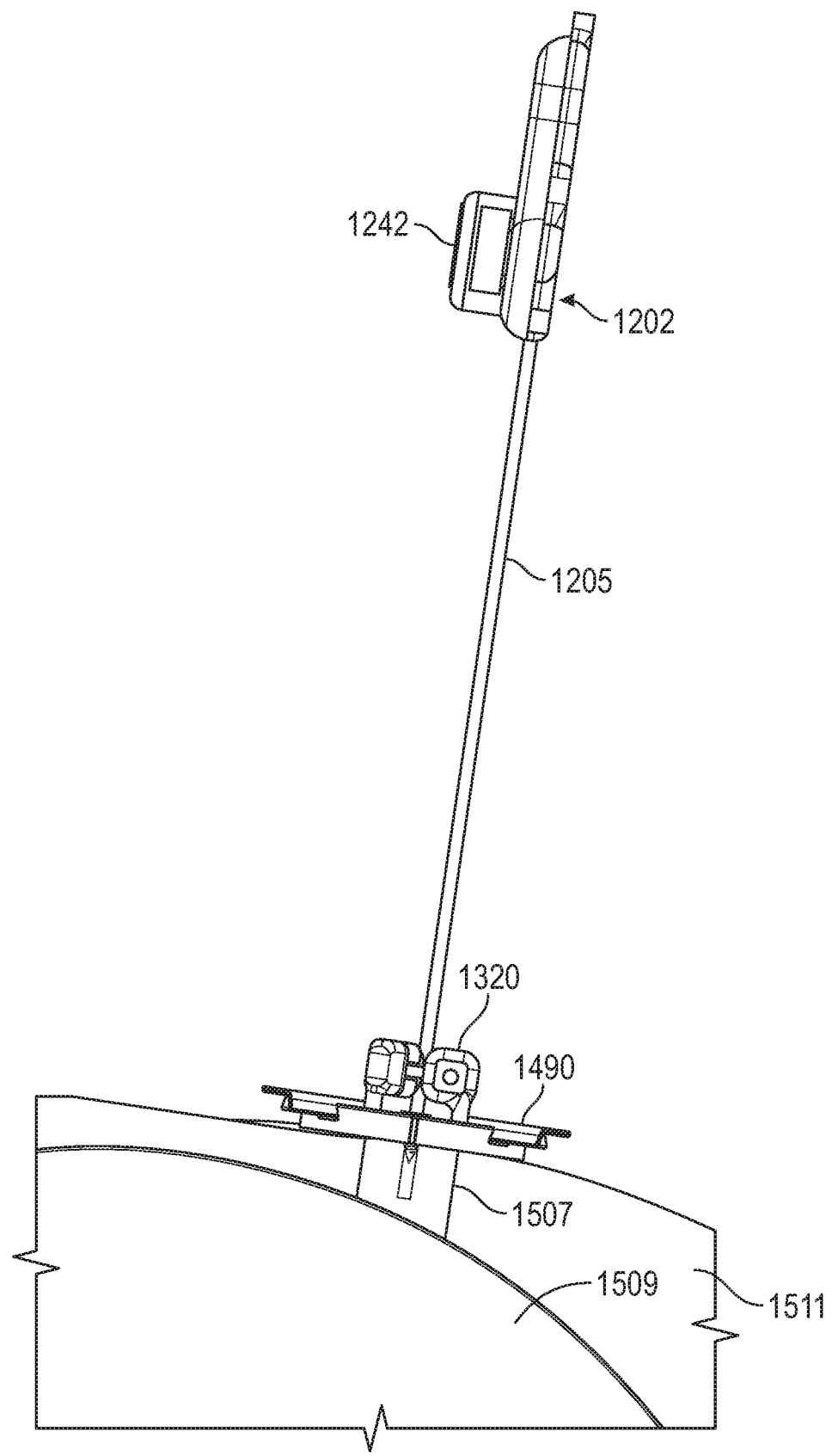
FIGS. 15A-15E illustrate various states of an example DBS system during and after positioning of the tip of the adjustable lead.
Figure 15B:
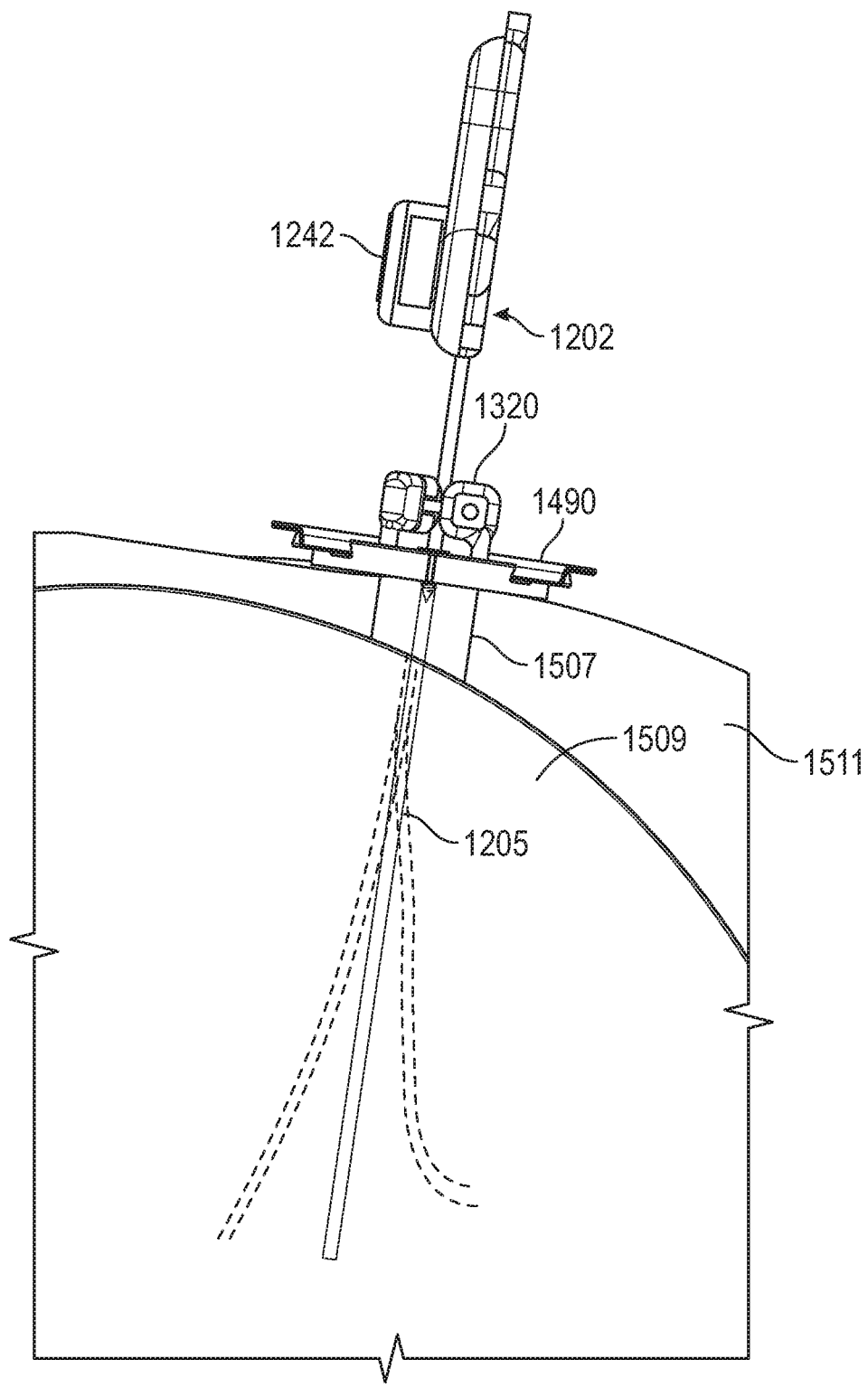

FIGS. 15A-15E illustrate various states of an example DBS system during and after positioning of the tip of the adjustable lead 1205. FIG. 15A illustrates generally early stages of the adjustable lead being inserted into the brain of a patient 1509 through a burr hole 1507 within the head 1511 of the patient. In addition to the adjustable lead 1205, the DBS system can include a burr hole plate 1490, and insertion device 1320, the implant 1202 and a motor control module 1242. FIG. 15B illustrates generally various progressions an insertion procedure can take as the adjustable electrode 1205 is inserted. The insertion device 1320 can provide the insertion motion to the adjustable lead 1205 and the motor control module 1242 and steering mandrels and pull wires of the implant 1202 can steer the tip of the adjustable electrode 1205.

Figure 15C:
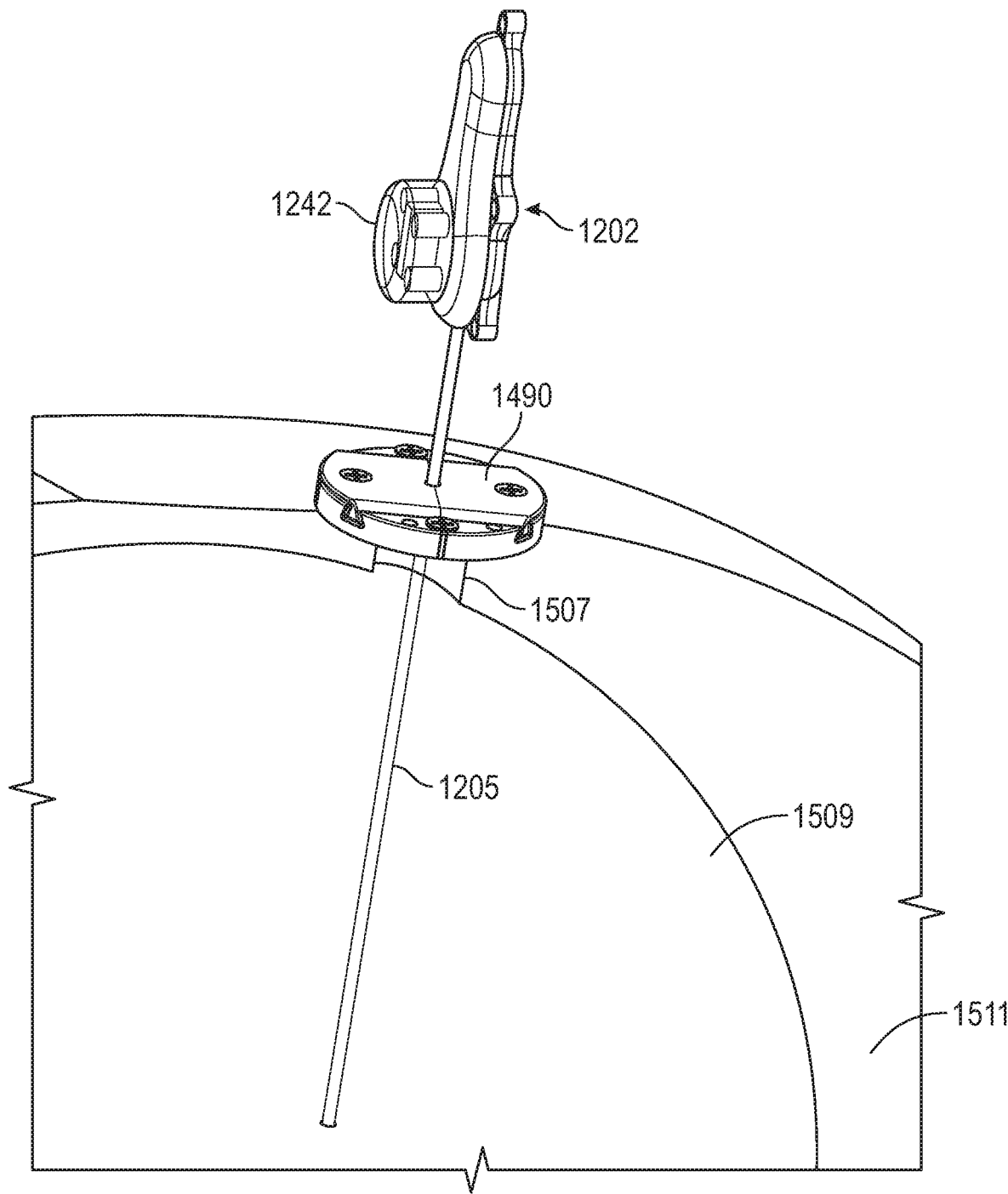
Figure 15D:
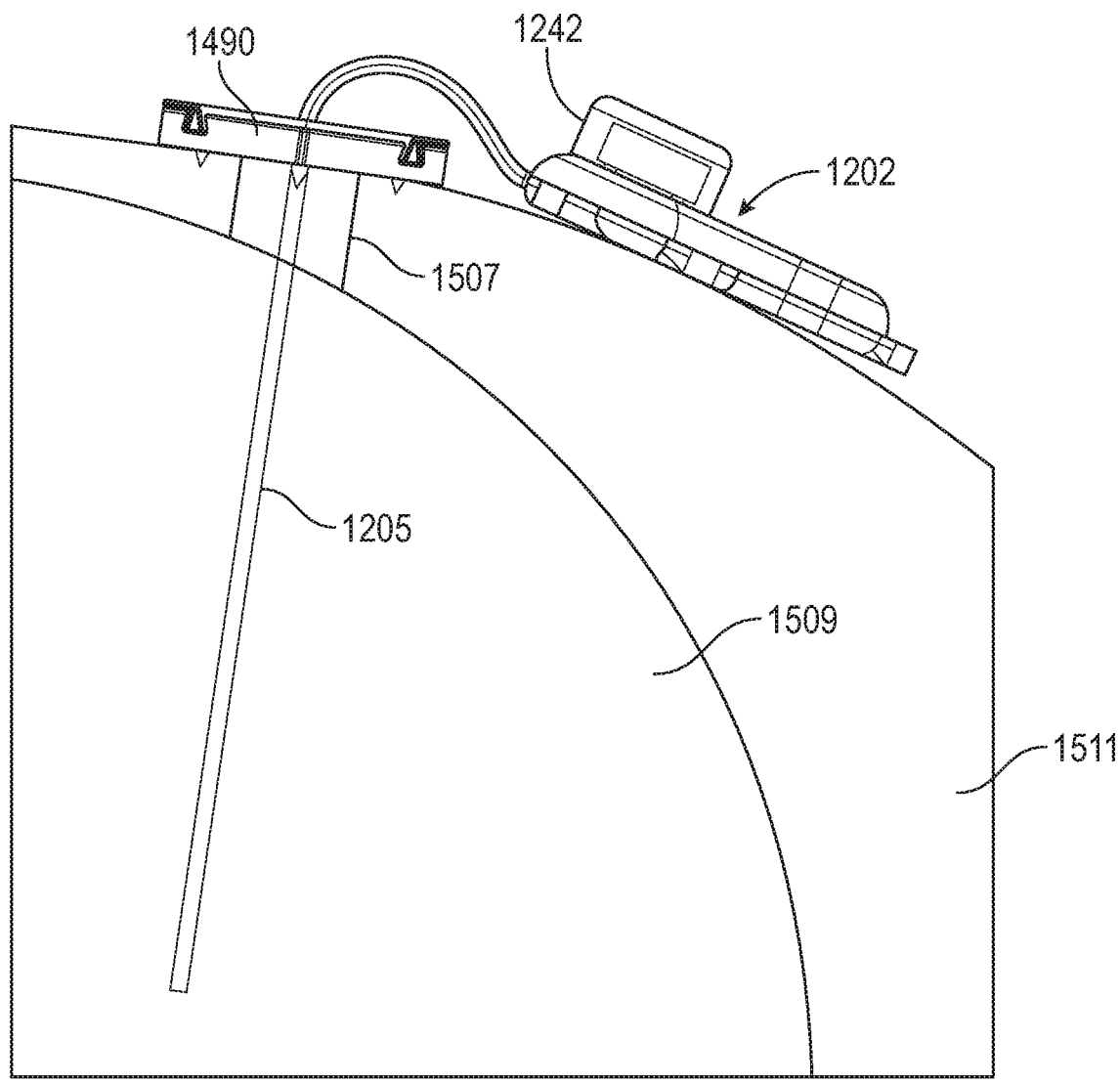
Figure 15E:
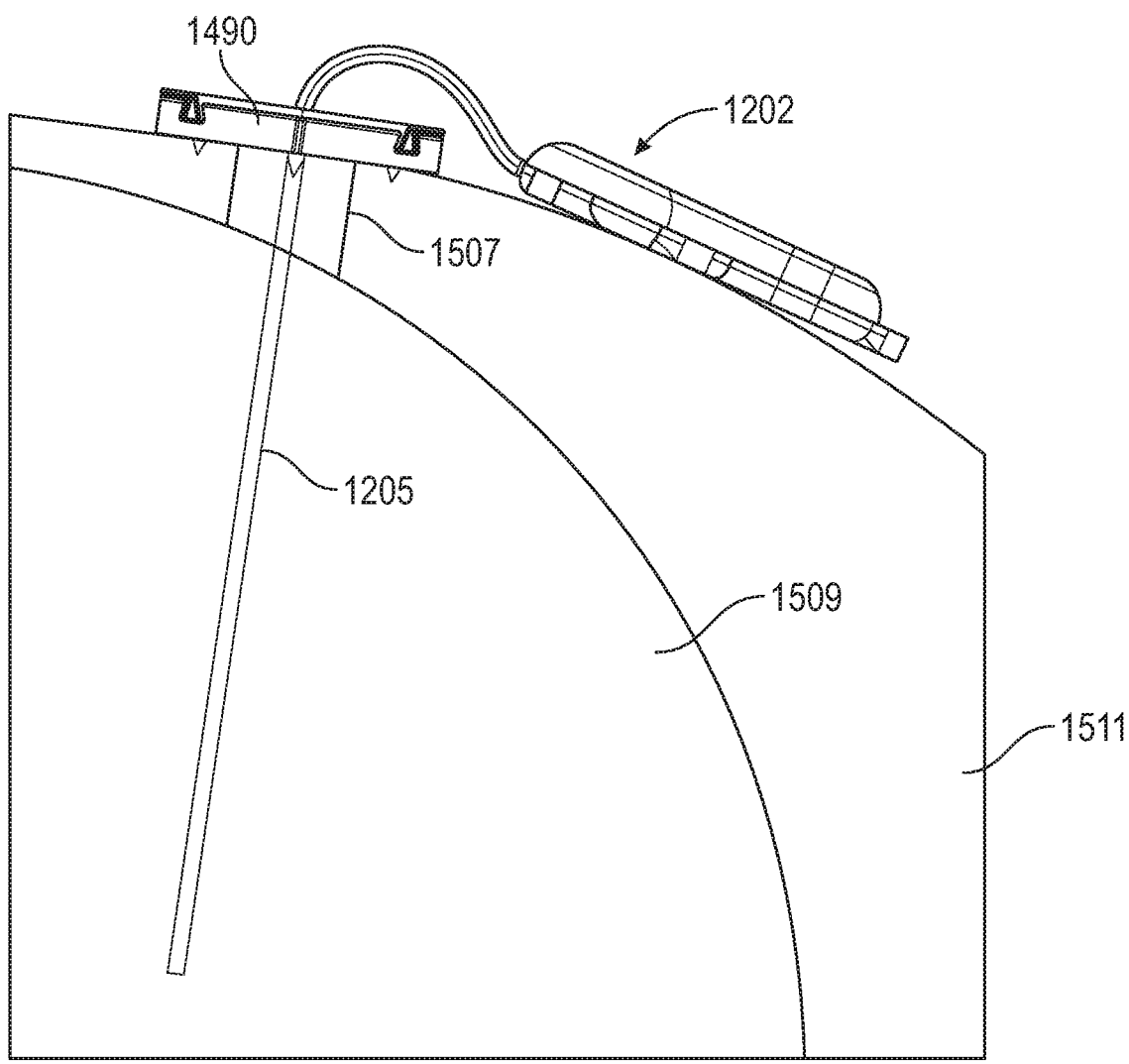

FIG. 15C illustrates generally a state of the DBS system soon after the tip of the adjustable lead 1205 has been positioned in a desired location within the brain 1509 of the patient. The insertion device 1320 has been removed from the burr hole plate 1490, and the slides 1492, 1497 have been closed and secured to fix the adjustable lead 1205. FIG. 15D illustrates the implant 1202 after being placed in the implant position. The motor control module 1242 remains connected to the implant 1202 while the implant 1202 is placed in the implant position to assist with the placement using the pull wires of the implant 1202. Once placed and secured in the implant position, the motor control module 1492 can be removed from the implant 1202 as shown in FIG. 15E. The surgical site of the implant 1202, exposed portion of the adjustable lead 1205 and the burr hole plate can be closed within skin of the patient. If adjustments to electrode position are desired or needed to optimize implant or electrode orientation after procedure completion and skin closure, the percutaneous motor module 1242 can be utilized to re-access and engage the implant 1202 and adjustable lead 1205 to modify the electrode positions or location within the body toward a target site or electrophysiological response.

Figure 16:
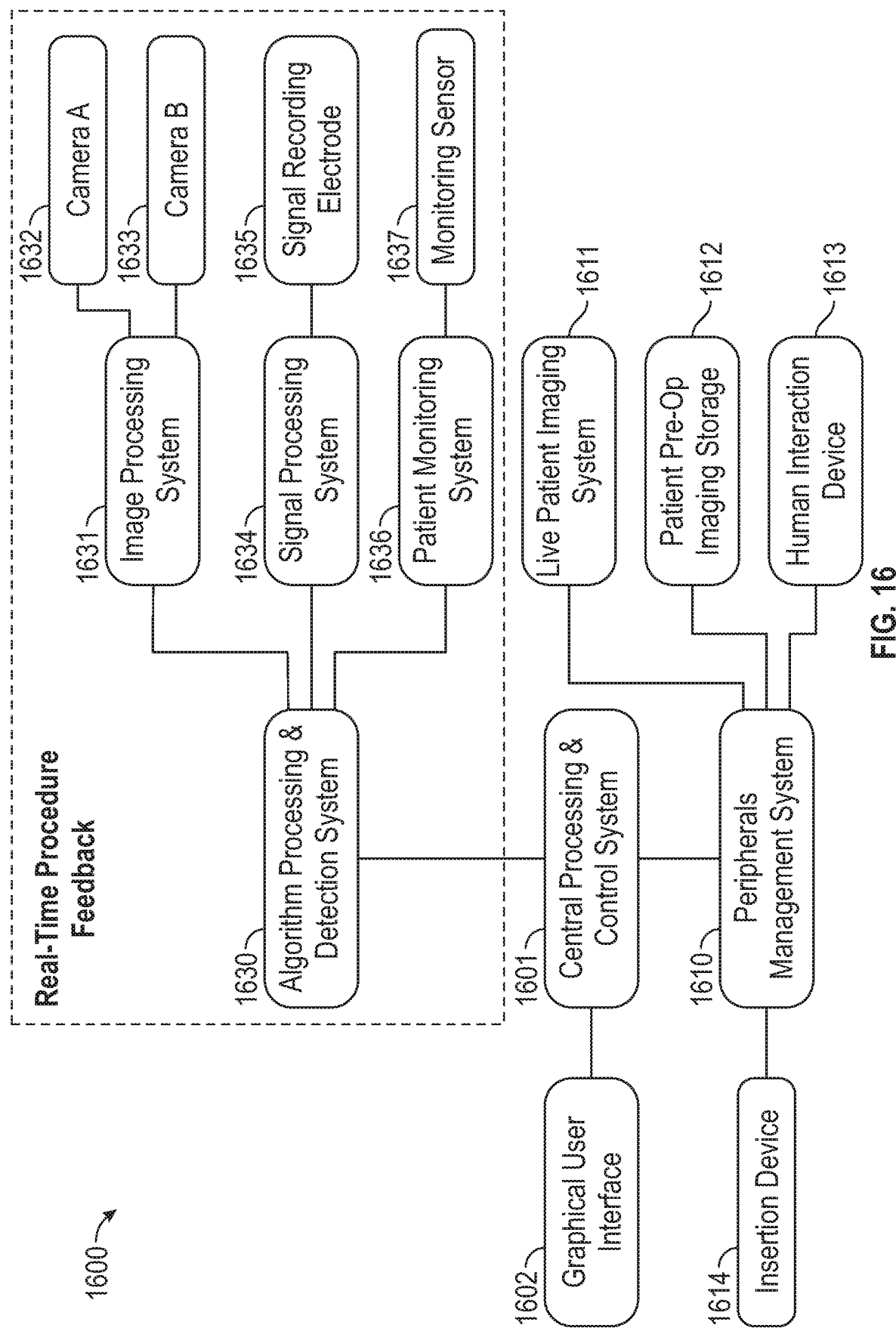
FIG. 16 is a block diagram illustrating a surgical insertion vision and control system for inserting a stimulation electrode within a patient, in accordance with an example embodiment of the present disclosure.

FIG. 16 is a block diagram illustrating a surgical insertion vision and control system 1600 for inserting a stimulation electrode within a patient, in accordance with an example embodiment of the present disclosure. The surgical system 1600 can include a central processing and control system 1601 for storing and updating procedure settings, configuration, and display. The surgical system 1600 can include a graphical user interface 1602 for adjusting view and other procedure settings. the graphical user interface can display information to user such as multi-dimensional anatomy images, cross-sectional anatomy images, insertion position graphics, buttons, etc. The surgical system 1600 can include a peripheral management system 1610 for managing communication with user-connected devices used for supplying information to, or interacting with, the surgical system. The peripheral management system 1610 can interface with a live patient imaging system 1611, a patient pre-op imaging system 1612, and a human interaction device 1613 among other things. The live patient imaging system 1611 can provide data used for real-time (live) imaging for visualization and target location information. Examples could include CT, MRI, Fluoroscopy. The patient pre-op imaging system 1612 can provide data used to create patient-specific visualizations and surgical templates. The human interaction device 1613 can include devices that allow a user of the surgical system 1600 to interact or control procedural actions and/or settings. Examples of such devices can include but are not limited to a foot pedal, a touchpad, a touchscreen, a hand-held controller or combinations thereof. The surgical system can include an insertion device 1614 such as the various components discussed above in FIGS. 1-15. The surgical system 1600 can include an algorithm and processing system 1630 that can provide real time feedback by applying algorithms and logic for determining surgical events and states. The surgical events and states can then be used as a feedback source for updating procedure settings and display. Parameters of the algorithm and processing system 1630 may include providing system parameter updates and modification based on object positional data over time, physiological patterns, or object angles relative to key points in the surgical site. The algorithm and processing system 1630 can interact with several subsystems including, but not limited to, an image processing system 1631, a signal processing system 1634, and a patient monitoring system 1636.

The image processing system 1631 can receive image information from a number of cameras or sensors such as a first camera 1632 in a position to view the surgical site such that it captures a left field, a second camera 1633 in a position to view the surgical site such that it captures the right field. The image processing system 1631 can process stereo camera imaging data from each camera view to create a multi-dimensional geometric map of the procedure site. A multi-dimensional geometric map can include detecting various objects in the view and can determine parameters such as location, angle, or distance of those objects in relation to one or more reference points. The signal processing system 1634 can interface with one or more instruments or sensors used to sense physiological signal waves of the patient and can include various electrodes 1635. The patient monitoring system 1636 can interface with one or more monitoring sensors 1637 to process data from the surgical suite, which can be fed back to a motor control algorithm during an insertion or positioning procedure. the one or more monitoring sensors can include, but are not limited to, an audio device, a video device, a nerve and muscular sensor, a tactical feedback device, a temperature sensor, a force sensor, or combinations thereof.

Figure 17:
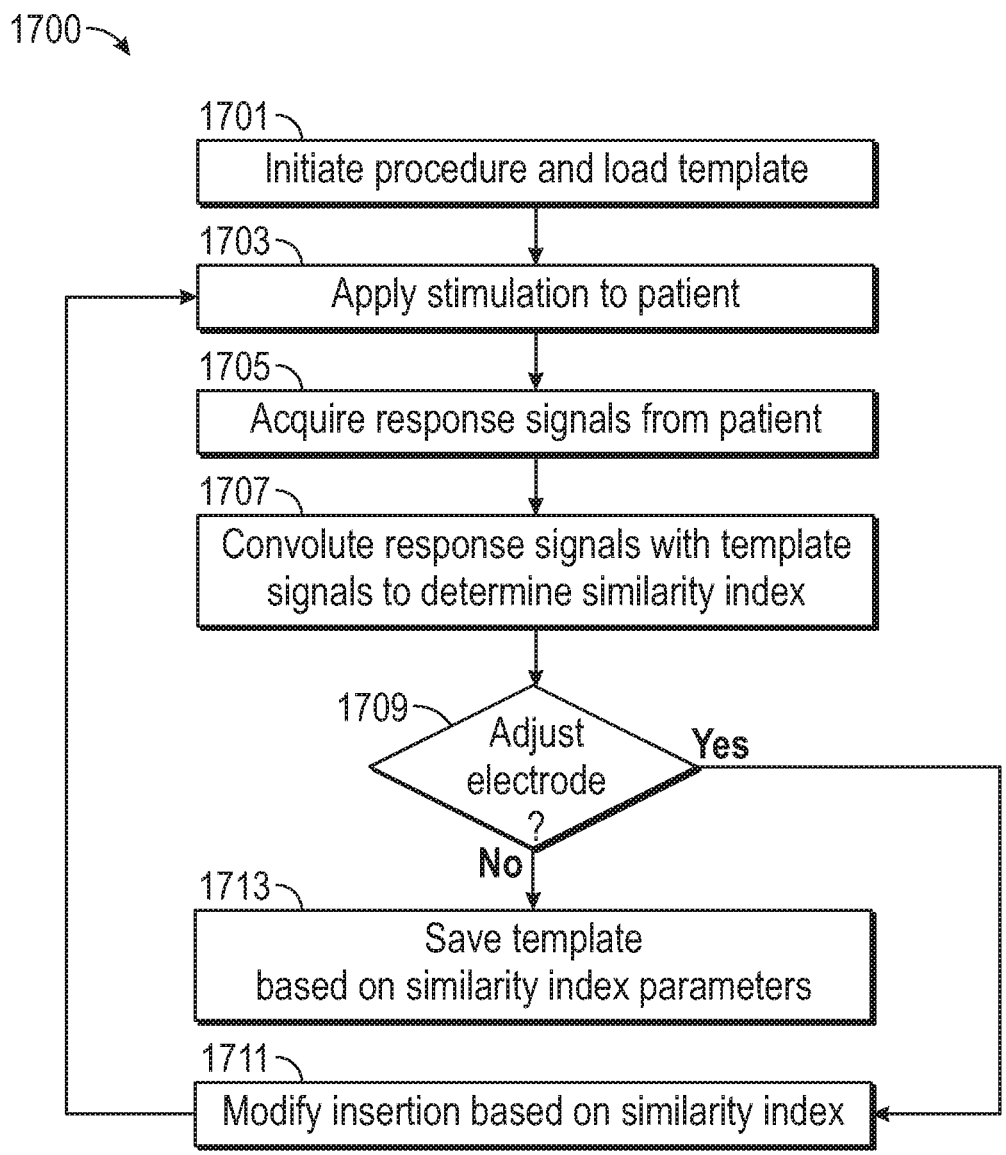
FIG. 17 illustrates generally an example method for inserting or positioning an adjustable electrode or steerable sheath and electrode combination according to the present subject matter.

FIG. 17 illustrates generally an example method 1700 for inserting or positioning an adjustable electrode or steerable sheath and electrode combination according to the present subject matter. At 1701, a procedure can be initiated via a graphical user interface for example. Initiation may include selecting a template for electrophysiological response signals, template signals, such as a template saved in a previous procedure for the patient. At 1703, optional stimulation can be applied to the patient such as via one or more electrodes, such as the inserted electrode. In some examples, the stimulation can be sound stimulation. In some examples, artificial stimulation of the patient is not provided and a response signal can be a continuously occurring or non-evoked response signal. An evoked response signal is an electrophysiological signal which is emitted in response to the optional stimulus or stimuli. At 1705, electrophysiological signals, response signals, can be acquired from the patient whether optional stimulation has been applied to the patient or not. In certain examples, acquisition of the response signals can include applying signal conditioning such as filtering, windowing, amplification, or combinations thereof. In some examples, the response signals can be digitized and transmitted to a central processing computer such as a processor of the algorithm processing and detection system 1630 of FIG. 16, for example. At 1707, the response signals or response signal data can be convolved with the template signals to identify or determine a similarity index with the template. In certain examples, the convolution can further include filtering and evaluating temporal or frequency trajectories of the similarity index collected over time to identify trends, magnitude, maxima, minima, etc. In certain examples, a correlation algorithm can be used to determine a similarity index instead of a convolution algorithm. In some examples, a convolution algorithm and a correlation algorithm can be used to determine a similarity index between the template signals and the response signals. At 1709, parameters for modifying a position of orientation of the inserted electrode, during or after an insertion procedure, can be determined and evaluated for possible improvement. If improvement of the position or orientation of the electrode is possible, at 1711, the position or orientation of the inserted electrode can be modified in real-time during an insertion or repositioning procedure based on parameters determined from the similarity index and analysis thereof, and the method can repeat by continuing to stimulate the one or more electrodes at 1703. If an optimal position has been established, the positioning and evaluation parameters can be stored as a template or can be used to update the existing template and template signals at 1713.

The pattern match algorithm for real-time surgical robotics decision adaptation described here improves this process by calculating and determining a value for a recorded signal measurement that signifies if the ongoing electrophysiological signal levels are changing overtime or throughout a clinical procedure. The algorithm improves the robotic surgical systems decision making and matrix tree. Existing electrophysiological recording methods can be less robust to environmental electrical noise and recording set parameters. In the operating room environment setting, where multiple electrical devices are present and the noise environment is an unknown and constantly variable, such robustness can improve procedure efficiency by avoiding inconsistent and unreliable electrophysiological patient recordings. For example, the current art algorithms are based exclusively on the Fast Fourier Transform method which must be tuned to specific acquisition rates and signal window length prior to or during the recording procedure in order to achieve specific resolutions in the desired electrophysiological frequency domain. The pattern match algorithm for real-time surgical robotics decision adaptation described here is less susceptible to environmental electrical noise and minimizes the need to modify, set, or adjust the signal window length and acquisition rate during the procedure. The method described herein, therefore, enables real-time analysis of electrophysiological data and prevents data loss—making it useful in a high noise, clinical environment with surgical robotic decision making.

In a first example, Example 1, a system for robotically assisted manipulation of an elongate member in a patient can include a drive wheel assembly configured to insert and retract the elongate member into and out of the patient; a steering assembly configured to shape the path and geometry of the elongate member; and a first control circuit communicatively coupled to the drive wheel assembly and the steering assembly and configured to control motion of the drive wheel assembly and the steering assembly to position a tip of the elongate member to a desired implantation site.

In Example 2, the subject matter of Example 1 includes, wherein the steering assembly includes a second control circuit coupled to the drive wheel assembly and the first control circuit; and wherein the drive wheel is configured to frictionally move the elongate member in response to a motion control signal of the first control circuit.

In Example 3, the subject matter of Example 2 includes, wherein the second control circuit is configured to generate drive signals to electrically drive an electrode of the elongate member for neurostimulation of the patient.

In Example 4, the subject matter of Examples 1-3 includes, wherein the steering assembly includes multiple steering mandrels, the multiple steering mandrels configured to wind and unwind pull wires coupled to a sheath positioned between the steering assembly and the drive wheel assembly, the sheath configured to guide lateral positioning of the tip of the elongate member as the wheel assembly inserts or retracts the elongate member.

In Example 5, the subject matter of Example 4 includes, a motor drive circuit configured to mechanically and percutaneously connect with the steering assembly during manipulation of the elongate member and to provide electromotive force to move the multiple steering mandrels.

In Example 6, the subject matter of Examples 1-5 includes, wherein the steering assembly includes multiple steering mandrels, the multiple steering mandrels configured to wind and unwind pull wires coupled to the elongate member, to guide lateral positioning of the tip of the elongate member as the drive wheel assembly inserts or retracts the elongate member; wherein the drive wheel assembly is housed with the steering assembly; wherein the motor drive circuit is configured to percutaneously and mechanically connect with the drive wheel and provide electromotive force to the drive wheel to insert and retract the elongate member within the patient; and wherein the motor drive circuit is configured to disconnect from the steering assembly and the drive wheel assembly in response to completion of manipulation of the elongate member.

In Example 7, the subject matter of Examples 1-6 includes, wherein an electrode of the elongate member is configured to stimulate nerves within a spine of patient.

In Example 8, the subject matter of Examples 1-7 includes, wherein an electrode of the elongate member is configured to stimulate nerves within a brain of the patient.

Example 9 is a system for robotically assisted manipulation of an implant in a patient, the system comprising: an implant-positioning unit, including a drive head and a steerable sheath configured to engage an electrode of the implant and robotically deliver and position and shape a path of the electrode along a target implantation path; and a control console communicatively coupled to the implant-positioning unit, the control console including a controller circuit configured to generate a motion control signal for controlling the implant-positioning unit to robotically deliver and position the implant into the target implantation site.

In Example 10, the subject matter of Example 9 includes, wherein the steerable sheath includes a plurality of pull wires configured to steer a geometry and curvature of a path of the steerable sheath.

In Example 11, the subject matter of Example 10 includes, wherein the implant positioning unit includes multiple mandrels coupled to the plurality of pull wires.

In Example 12, the subject matter of Example 11 includes, wherein the implant positioning unit includes a first drive wheel configured to engage an outside surface of the electrode and to apply insertion force to the electrode.

In Example 13, the subject matter of Example 12 includes, wherein the implant positioning unit includes a second drive wheel configured to engage the outside surface of the electrode opposite the first drive wheel.

In Example 14, the subject matter of Example 13 includes, wherein the implant positioning unit includes actuators to vertically offset the first drive wheel and the second drive wheel to rotate electrode about an axis parallel to a major direction of the insertion force.

In Example 15, the subject matter of Examples 13-14 includes, a motor control unit including multiple actuators configured to percutaneously engage the mandrels and to apply torque to the mandrels to control extension and retraction of the pull wires responsive to the control console.

Example 16 is a method of manipulating an electrode for stimulation of nerves of a patient, the method comprising: initiating a procedure to modify a position of an electrode; receiving either evoked electrophysiological signals from the patient or non-evoked electrophysiological signals from the patient; convolving the electrophysiological signals with template signals to generate a similarity index; and modifying a position of the electrode based on the similarity index deviating from a threshold.

In Example 17, the subject matter of Example 16 includes, wherein modifying a position of the electrode includes generating a motion command signal based on the similarity index.

In Example 18, the subject matter of Example 17 includes, wherein modifying a position of the electrode includes receiving the motion command signal at a motor control module coupled to a drive wheel; and moving the drive wheel in response to the motion command signal to further insert or retract the electrode from a current implant location of the patient.

In Example 19, the subject matter of Example 18 includes, wherein the motion command signal is based on an input signal received from a camera system, a radiographical tracking system, or a human interaction device.

In Example 20, the subject matter of Examples 17-19 includes, wherein modifying a position of the electrode includes receiving the motion command signal at a motor control module coupled to a drive wheel; and wherein modifying a position of the electrode includes rotating the electrode, based on the motion command signal, about a longitudinal axis parallel to the electrode.

In Example 21, the subject matter of Examples 17-20 includes, wherein modifying a position of the electrode includes receiving the motion command signal at a percutaneous motor control module coupled to an implanted drive wheel motor.

Example 22 is at least one machine-readable medium including instructions that, when executed by processing circuitry, cause the processing circuitry to perform operations to implement of any of Examples 1-21.

Example 23 is an apparatus comprising means to implement of any of Examples 1-21.

Example 24 is a system to implement of any of Examples 1-21.

Example 25 is a method to implement of any of Examples 1-21.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for robotically assisted manipulation of an elongate member in a patient, the system comprising:
   implantable elongate member positioning device comprising:
   an implantable housing including trocar access channels and self-sealing septums;
   a drive wheel assembly configured to insert and retract the elongate member into and out of the patient; and
   a percutaneous motor module couplable to the implantable elongate member positioning device via the trocar access channels and the self-sealing septums, the percutaneous motor module including a first control circuit configured to control motion of the drive wheel assembly to position a tip of the elongate member to a desired implantation site,
   wherein the implantable elongate member positioning device includes a second control circuit communicatively coupled to the first control circuit; and
   wherein the second control circuit is configured to generate drive signals to electrically drive an electrode of the elongate member for electrical stimulation of the patient.

2. The system of claim 1, wherein the drive wheel is configured to frictionally move the elongate member in response to a motion control signal of the first control circuit.

3. The system of claim 1, wherein an electrode of the elongate member is configured to stimulate nerves within a spine of patient.

4. The system of claim 1, wherein an electrode of the elongate member is configured to stimulate nerves within a brain of the patient.

5. A system for robotically assisted manipulation of an implant in a patient, the system comprising:
   an implant-positioning unit implantable under skin of a patient, the implant-positioning unit including an implantable housing containing a drive head and a steerable sheath configured to engage an electrode of the implant and robotically deliver and position and shape a path of the electrode along a target implantation path, wherein the implantable housing includes a trocar entrance and a self-sealing septum; and
   a percutaneous motor module couplable through the skin to the implant-positioning unit through the trocar entrance and the self-sealing septum, the percutaneous motor module including a control console communicatively coupled to the implant-positioning unit, the control console including a controller circuit configured to generate a motion control signal for controlling the implant-positioning unit to robotically deliver and position the implant into a target implantation site,
   wherein the implant positioning unit includes a first drive wheel configured to engage an outside surface of the electrode and to apply insertion force to the electrode, and
   wherein the implant positioning unit includes a second drive wheel configured to engage the outside surface of the electrode opposite the first drive wheel.

6. The system of claim 5, wherein the steerable sheath includes a plurality of pull wires configured to steer a geometry and curvature of a path of the steerable sheath.

7. The system of claim 6, wherein the implant positioning unit includes multiple mandrels coupled to the plurality of pull wires.

8. The system of claim 5, wherein the implant positioning unit includes actuators to vertically offset the first drive wheel and the second drive wheel to rotate electrode about an axis parallel to a major direction of the insertion force.

9. The system of claim 5, wherein the percutaneous motor module includes multiple actuators configured to percutaneously engage the mandrels via a plurality of trocar access channels and to apply torque to the mandrels to control extension and retraction of the pull wires responsive to the control console.

10. A system for manipulation of an implant in a patient, the system comprising:
- an implant-positioning unit implantable under skin of a patient, the implant-positioning unit including a drive head configured to engage an electrode of the implant and position the electrode along a target implantation path, the implant-positioning unit including an implantable housing including a trocar access channel and a self-sealing septum configured to enable access to the drive head; and
- a percutaneous access mechanism including a trocar couplable through the skin to engage a portion of the drive head within the implant-positioning unit, the percutaneous access mechanism configured to manipulate the drive head via the trocar access channel and self-sealing septum,
- wherein the drive head includes a first drive wheel configured to engage an outside surface of the electrode and to apply insertion force to the electrode, and
- wherein the drive head includes a second drive wheel configured to engage the outside surface of the electrode opposite the first drive wheel.

11. The system of claim 10, wherein the percutaneous access mechanism includes a percutaneous motor module, the percutaneous motor module includes multiple actuators configured to percutaneously engage the drive head via a plurality of trocar access channels and to apply torque to the drive head to control extension and retraction of the electrode.

12. The system of claim 10, wherein the implantable housing including an electrode chamber to retain an excess length of the electrode.

13. The system of claim 10, wherein the drive head includes a pair of friction wheels engaging the electrode.

14. The system of claim 10, wherein the implant-positioning unit includes a steering assembly configured to shape a path and geometry of the electrode.

* * * * *